United States Patent
Hosokawa et al.

(10) Patent No.: US 12,313,639 B2
(45) Date of Patent: May 27, 2025

(54) PARTICLE CONFIRMING METHOD, PARTICLE TRAPPING CHIP, AND PARTICLE ANALYZING SYSTEM

(71) Applicant: Sony Corporation, Tokyo (JP)

(72) Inventors: Hiroyuki Hosokawa, Kanagawa (JP); Tasuku Yotoriyama, Tokyo (JP); Shin Masuhara, Tokyo (JP); Isamu Nakao, Kanagawa (JP)

(73) Assignee: Sony Corporation, Tokyo (JP)

( * ) Notice: Subject to any disclaimer, the term of this patent is extended or adjusted under 35 U.S.C. 154(b) by 266 days.

(21) Appl. No.: 16/970,307

(22) PCT Filed: Nov. 11, 2019

(86) PCT No.: PCT/JP2019/044100
§ 371 (c)(1),
(2) Date: Aug. 14, 2020

(87) PCT Pub. No.: WO2020/129462
PCT Pub. Date: Jun. 25, 2020

(65) Prior Publication Data
US 2021/0364410 A1    Nov. 25, 2021

(30) Foreign Application Priority Data
Dec. 21, 2018  (JP) .................. 2018-240079

(51) Int. Cl.
*C12Q 1/6813*    (2018.01)
*G01N 15/14*    (2024.01)
(Continued)

(52) U.S. Cl.
CPC ..... *G01N 35/00584* (2013.01); *C12Q 1/6813* (2013.01); *G01N 15/1429* (2013.01); *G06V 20/693* (2022.01); *G06V 20/695* (2022.01)

(58) Field of Classification Search
CPC .. B01L 13/02; B01L 3/52; B01L 3/505; B01L 7/00; B01L 2035/00435;
(Continued)

(56) References Cited

U.S. PATENT DOCUMENTS

| 8,691,151 B2 * | 4/2014 | Kovac | B01L 3/502761 436/63 |
| 2005/0026181 A1 * | 2/2005 | Davis | C12Q 1/6876 435/6.13 |

(Continued)

FOREIGN PATENT DOCUMENTS

| CA | 2015983 A1 | 11/1990 |
| CA | 2189486 A1 | 5/1998 |

(Continued)

OTHER PUBLICATIONS

International Written Opinion and English translation thereof mailed Dec. 24, 2019 in connection with International Application No. PCT/JP2019/044100.

(Continued)

*Primary Examiner* — Jill A Warden
*Assistant Examiner* — Michael Stanley Gzybowski
(74) *Attorney, Agent, or Firm* — Wolf, Greenfield & Sacks, P.C.

(57) ABSTRACT

To provide a technology for confirming that a desired particle is recovered in single cell analysis.
The present technology provides a particle confirming method including a correlating step of correlating ID information possessed by a particle trapped in a well in a particle trapping region with position information of the well, a discharging step of discharging the particle from the well, an ID information acquiring step of acquiring ID information of the particle after the discharging step, and a confirming step of confirming the position of the well in which the particle (Continued)

has been trapped, on the basis of the acquired ID information. In addition, the present technology also provides a particle trapping chip and a particle analyzing system to be used for carrying out the method.

14 Claims, 11 Drawing Sheets

(51) Int. Cl.
*G01N 15/1429* (2024.01)
*G01N 35/00* (2006.01)
*G06K 9/32* (2006.01)
*G06K 9/46* (2006.01)
*G06K 9/62* (2022.01)
*G06V 20/69* (2022.01)

(58) Field of Classification Search
CPC ......... B01L 2300/042; B01L 2300/069; B01L 2300/105; B01L 2300/1844; G01N 1/34; G01N 1/42; G01N 335/10; G01N 35/00584; G01N 2030/143
See application file for complete search history.

(56) References Cited

U.S. PATENT DOCUMENTS

| | | | |
|---|---|---|---|
| 2009/0258383 A1 | 10/2009 | Kovac | |
| 2019/0026536 A1 | 1/2019 | Matsubara | |
| 2019/0031993 A1 | 1/2019 | Matsunaga et al. | |
| 2019/0039070 A1 | 2/2019 | Matsunaga et al. | |
| 2019/0264159 A1* | 8/2019 | Matsumoto | ............ C12M 47/04 |

FOREIGN PATENT DOCUMENTS

| | | | | |
|---|---|---|---|---|
| CN | 103674814 A | | 3/2014 | |
| CN | 104350374 A | | 2/2015 | |
| CN | 105164246 A | | 12/2015 | |
| CN | 108291863 A | | 7/2018 | |
| CN | 108387505 A | | 8/2018 | |
| CN | 108601505 A | | 9/2018 | |
| CN | 108780035 A | | 11/2018 | |
| EP | 3438238 A1 | | 2/2019 | |
| EP | 3438644 A1 | | 2/2019 | |
| EP | 3438662 A1 | | 2/2019 | |
| JP | H05-2408 U | | 1/1993 | |
| JP | H05-240869 A | | 9/1993 | |
| JP | 2007500013 A | | 1/2007 | |
| JP | 2018-143135 A | | 9/2018 | |
| WO | WO-9967641 A2 * | 12/1999 | ........... A61K 31/428 |
| WO | WO-2015095395 A1 | | 6/2015 | |
| WO | WO 2017/169770 A1 | | 10/2017 | |
| WO | WO 2017/170994 A1 | | 10/2017 | |

OTHER PUBLICATIONS

International Preliminary Report on Patentability and English translation thereof mailed Jul. 1, 2021 in connection with International Application No. PCT/JP2019/044100.

International Search Report and English translation thereof mailed Dec. 24, 2019 in connection with International Application No. PCT/JP2019/044100.

* cited by examiner

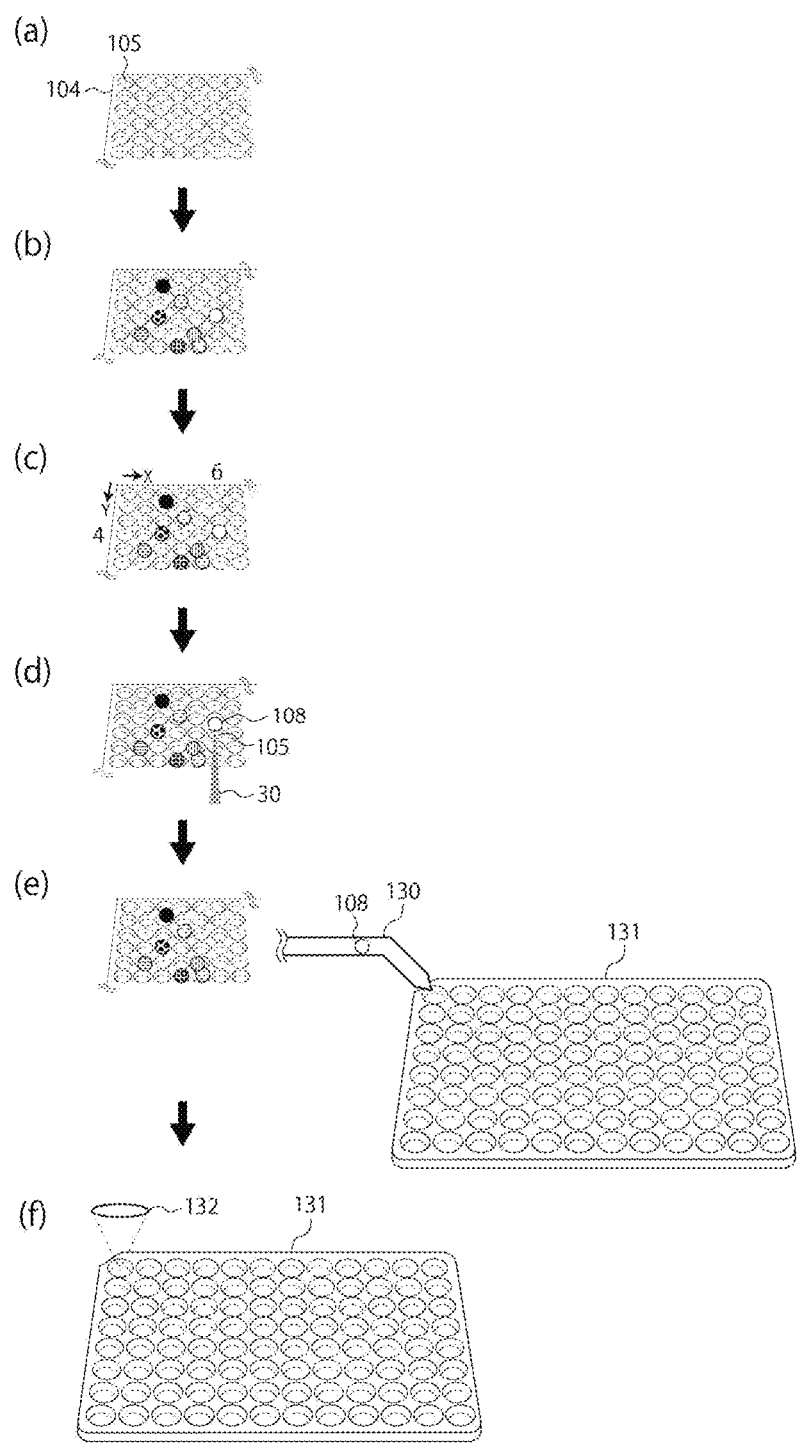

FIG.9
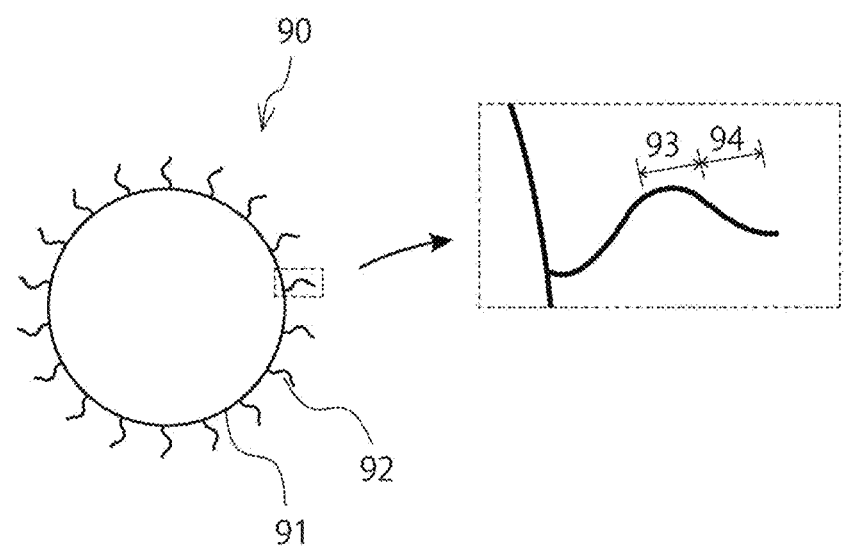
FIG.10
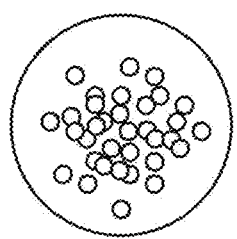 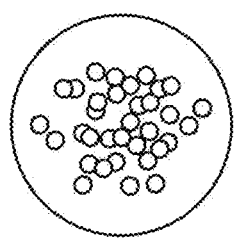 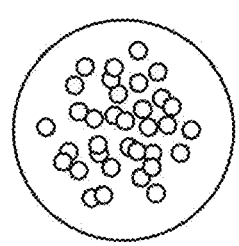

FIG.11
(a)
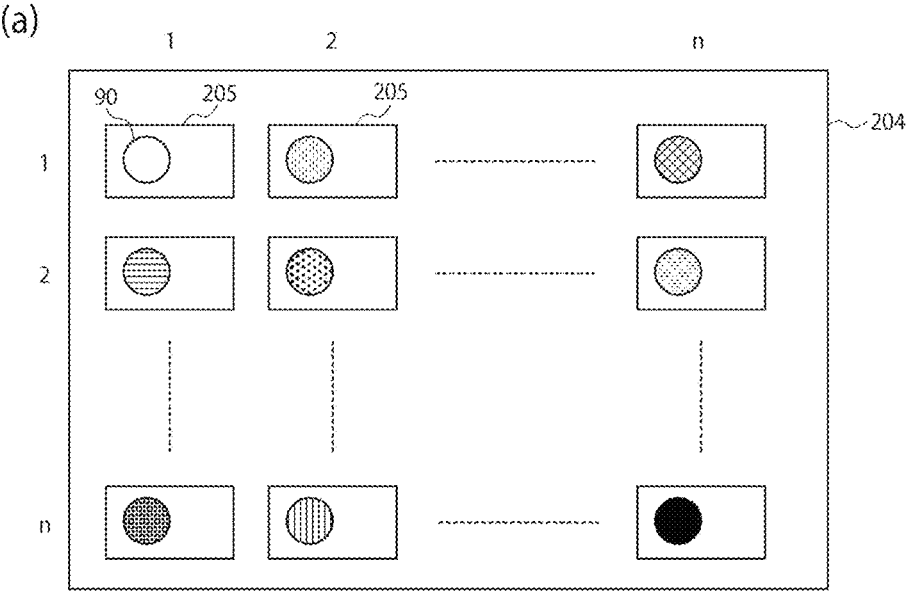
(b)
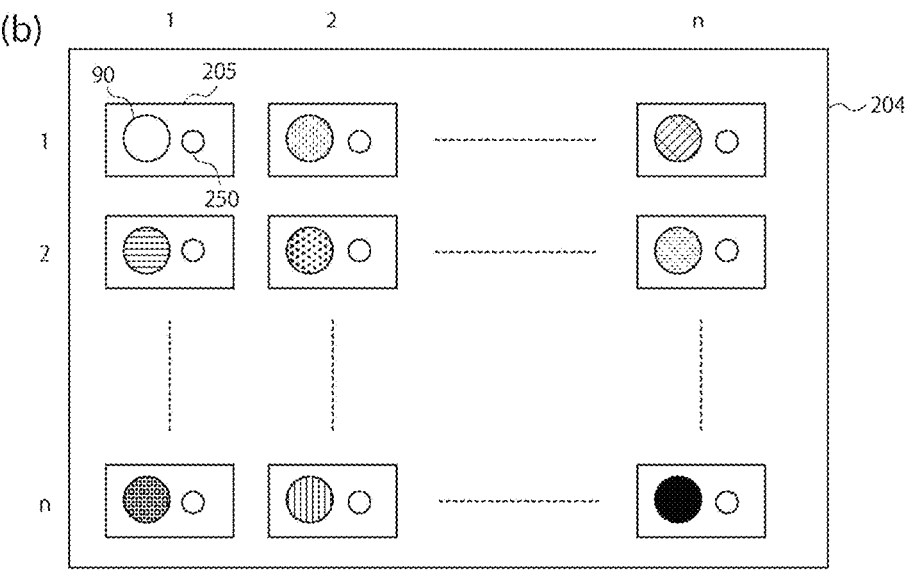

FIG.12
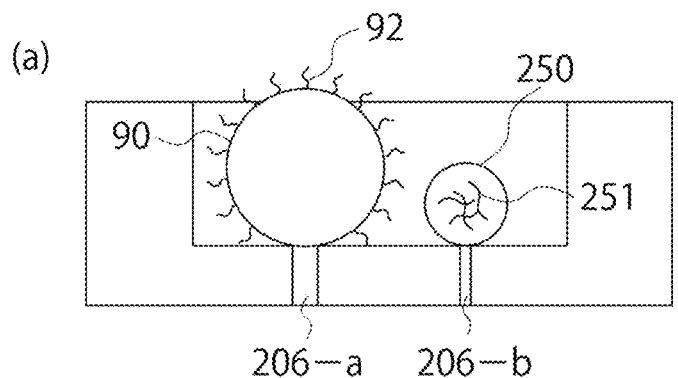
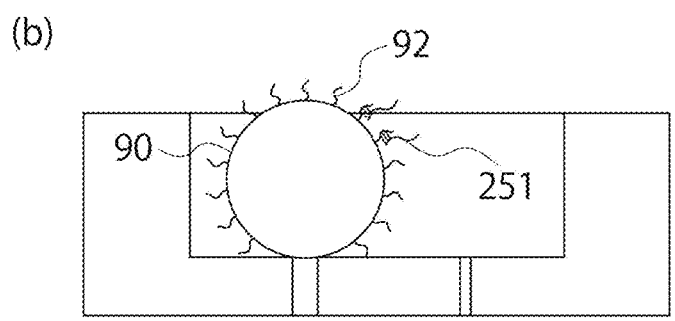
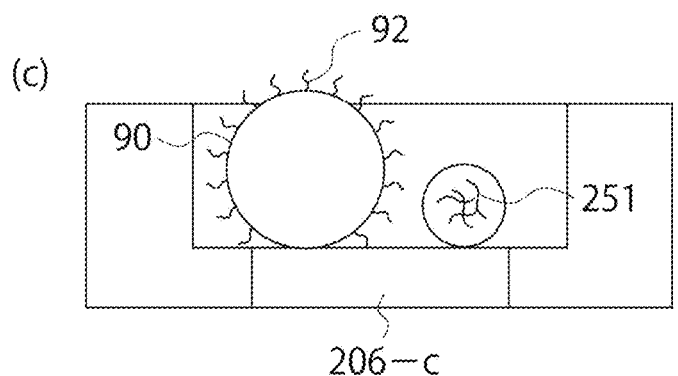
FIG.13
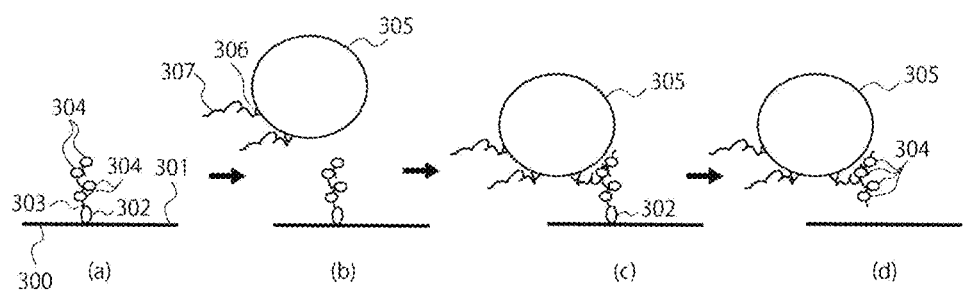

PARTICLE CONFIRMING METHOD, PARTICLE TRAPPING CHIP, AND PARTICLE ANALYZING SYSTEM

CROSS-REFERENCE TO RELATED APPLICATIONS

This application claims the benefit under 35 U.S.C. § 371 as a U.S. National Stage Entry of International Application No. PCT/JP2019/044100, filed in the Japanese Patent Office as a Receiving Office on Nov. 11, 2019, which claims priority to Japanese Patent Application Number JP2018-240079, filed in the Japanese Patent Office on Dec. 21, 2018, each of which is hereby incorporated by reference in its entirety.

TECHNICAL FIELD

The present technology relates to a particle confirming method, a particle trapping chip, and a particle analyzing system. More in detail, the present technology relates to a particle confirming method for confirming, after movement of particles conducted in particle analysis, that intended particles have been moved or positions of the particles before the movement, a particle trapping chip used for carrying out the particle confirming method, and a particle analyzing system for carrying out the particle confirming method.

BACKGROUND ART

A single cell analysis technology has been drawing attention. In the single cell analysis technology, trapping cells one by one respectively into a multiplicity of microwells arranged on a plane, and individually observing the forms of the respective cells and analyzing the characteristic of each cell, and/or analyzing reactions of the respective cells with reagents by using, for example, fluorescence or the like as an index, may be performed.

Hitherto, some technologies for performing single cell analysis have been proposed. For example, PTL 1 discloses a single cell analysis apparatus. The apparatus includes a substrate, a plurality of cell trapping holes provided in one surface of the substrate, a nucleic acid trapping region that is provided with a nucleic acid trapping body for trapping nucleic acids extracted from single cells trapped respectively in the cell trapping holes and that is disposed in the vicinity of the cell trapping holes, and a second hole provided in one surface of the substrate, in which the second hole is larger than the cell trapping holes (claim 1).

CITATION LIST

Patent Literature

PTL 1
JP 2018-143135A

SUMMARY

Technical Problems

For performing single cell analysis, a plate having a multiplicity of wells arranged on one surface may be used. In the case of performing single cell analysis by use of the plate, cells may be trapped respectively in the multiplicity of wells one by one, and, next, the characteristic of the cell in each well may be analyzed. For fractionating the cells recognized to have a desired characteristic by the analysis, the cells may be discharged from the wells in which the cells are trapped, and the cells may be moved from the plate to other region (for example, to a well plate or a container).

For confirming that the desired cells have been fractionated, it may be contemplated, for example, to trace the cells by a camera during the cell fractionating operation (that is, the discharge and the movement). Here, the distance from the plate to the other region is sometimes not included in one visual field of the camera observing the cells. Therefore, for confirming that the cells have been fractionated, the fractionating operation should be conducted while moving the visual field of the camera. However, the fractionating operation attended by the movement of the visual field of the camera needs time and labor. Particularly in the case where plural cells are to be fractionated successively, the fractionating operation involving the movement of the visual field of the camera is not suitable. In addition, in the case where tracing of the cells is not conducted, it may be impossible to confirm whether the desired cells have been fractionated.

It is a principal object of the present technology to provide a technique for confirming, after movement of particles conducted in particle analysis, that the intended particles have been moved or the positions of the particles before the movement.

Solution to Problems

The present inventors have found out that the above-mentioned problems can be solved by a specific particle confirming method, a specific particle trapping chip, and a specific particle analyzing system.

Specifically, the present technology provides a particle confirming method including a correlating step of correlating identification information possessed by a particle trapped in a well in a particle trapping region with position information of the well, a discharging step of discharging the particle from the well, an identification information acquiring step of acquiring identification information of the particle after the discharging step, and a confirming step of confirming whether the particle has been trapped in the well possessing the position information, on the basis of the acquired identification information.

The particle confirming method according to the present technology may further include a trapping step of trapping the particle through a linker fixed to the well in the particle trapping region.

The trapping step may include a labeling step of labeling the particle trapped in the well to impart identification information to the particle.

In the labeling step, the particle may be labeled with fluorescence, a color, an electric charge, a magnetic charge, an oligonucleic acid, or a peptide to impart identification information to the particle.

According to one embodiment of the present technology, in the labeling step, adjacent wells in the particle trapping region may have different label elements, and the particles trapped in the adjacent wells may be labeled with different label elements.

According to another embodiment of the present technology, in the labeling step, the wells in the particle trapping region may be arranged to form a plurality of rows or columns, the adjacent two rows or columns may have mutually different label elements, and the particles trapped in the wells in the adjacent rows or columns may be labeled with the different label elements.

The correlating step may further include an image acquiring step of acquiring an image of the particle trapping region, and fluorescence, a color, or a size or shape of a particle may be acquired from the image as identification information and the identification information and the position information may be correlated with each other.

In the discharging step, a plurality of particles having identification information may be discharged successively.

In the confirming step, an order of discharge of the plurality of particles may be referred to.

In the discharging step, the discharge may be temporarily stopped after a predetermined number of particles are discharged successively.

In the discharging step, a particle to be a mark may be discharged after a predetermined number of particles are discharged successively.

In the discharging step, two or more particles discharged successively may have different pieces of identification information.

According to a further embodiment of the present technology, the particle trapping region may be divided into a plurality of fields, and the well may include a label element for specifying the field in which the well is disposed.

According to one embodiment of the present technology, the discharging step may further include a light irradiation step of irradiating the linker fixed to the well with light to cut the linker.

According to one embodiment of the present technology, the particle confirming method may further include a particle moving step of causing the particle discharged from the well in the discharging step to pass through a channel, and, in the identification information acquiring step, the identification information may be acquired from the particle passing through the channel or the particle having passed through the channel.

According to one embodiment of the present technology, in the confirming step, a group of a predetermined number of successive particles may be disposed of when an order of pieces of identification information of the particles discharged in the discharging step and an order of pieces of identification information of the particles acquired in the identification information acquiring step are different from each other.

According to one preferred embodiment of the present technology, the particle confirming method of the present technology may further include a particle fractionating step.

According to another preferred embodiment of the present technology, the particle trapped in the well in the correlating step may have two or more different pieces of identification information.

According to a further preferred embodiment of the present technology, the particle confirming method of the present technology may further include a nucleic acid sequence step of acquiring identification information of the particle by a nucleic acid sequence treatment, in the identification information acquiring step.

In addition, the present technology also provides a particle trapping chip including a particle trapping region having at least one well, in which each of the at least one well has a label element that is able to be transferred from the well to a particle.

According to one embodiment of the present technology, the label element may be fixed to each well through a linker, and the fixation of the label element through the linker may be able to be canceled.

According to one embodiment of the present technology, adjacent wells in the particle trapping region may have different label elements.

According to another embodiment of the present technology, the wells in the particle trapping region may be arranged such as to form a plurality of rows or columns, and two adjacent rows or columns may have mutually different label elements.

Besides, the present technology also provides a particle analyzing system including a particle trapping chip that includes a particle trapping region having at least one well, each of the at least one well having a label element capable of being transferred from the well to a particle, a particle recovering section that recovers the particle discharged from the at least one well, and an identification information acquiring section that acquires identification information possessed by the discharged particle.

BRIEF DESCRIPTION OF DRAWINGS

FIG. 3 illustrates schematic diagrams for explaining a particle fractionating treatment including the particle confirming method according to the present technology.

FIG. 9 is a schematic diagram depicting an example of a particle having two or more different pieces of ID (Identification) information.

FIG. 10 illustrates diagrams for explaining a quantum dot used as a label element in the present technology.

FIG. 11 illustrates schematic diagrams for explaining a particle confirming treatment of the present technology.

FIG. 12 illustrates diagrams depicting a state in which a particle is trapped in a well.

FIG. 13 illustrates diagrams for explaining a coupling mode between a label element and a particle.

DESCRIPTION OF EMBODIMENTS

Figure 1:
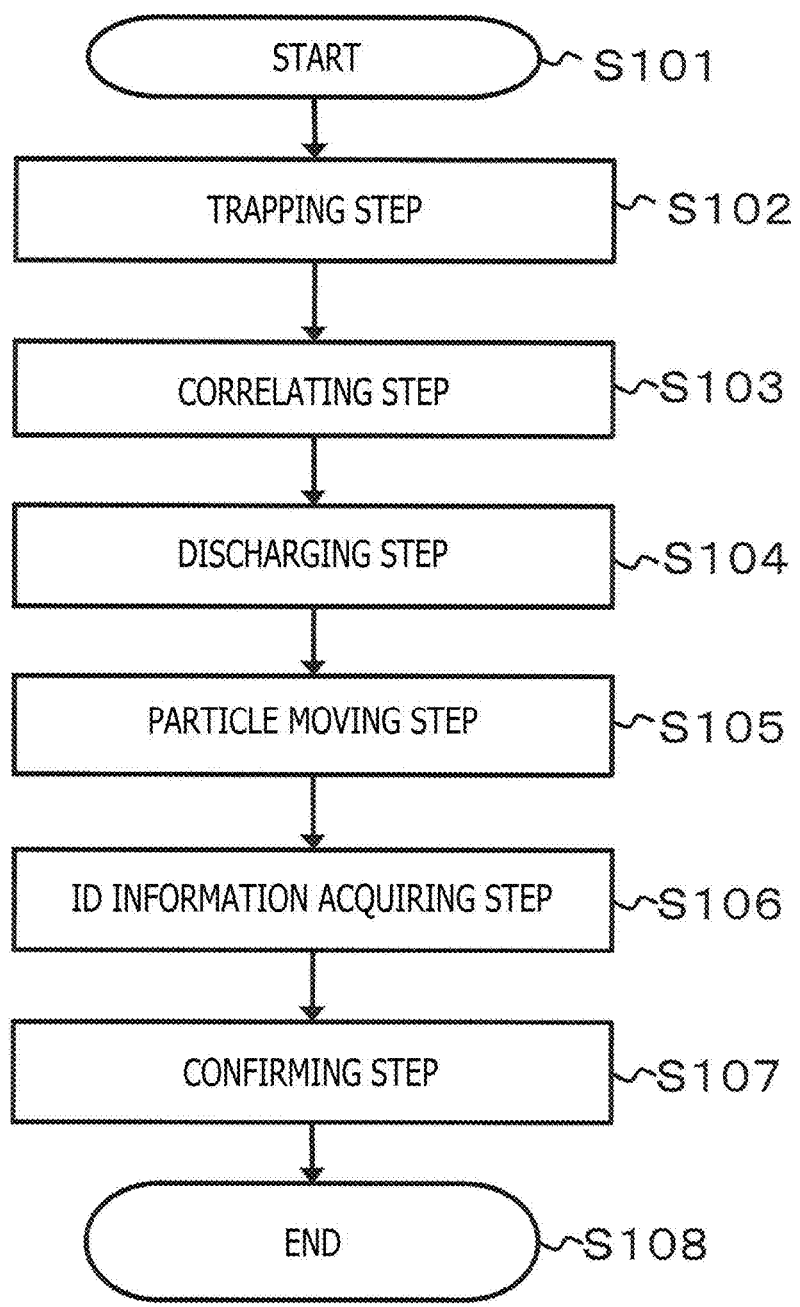
FIG. 1 is an example of a flow chart for a particle confirming method according to the present technology.

Preferred embodiments for carrying out the present technology will be described below. Note that the embodiments described below illustrate typical embodiments of the present disclosure, and the scope of the present disclosure is not construed as limited only to these embodiments. Note that the description of the present technology will be made in the following order.

1. First embodiment (Particle confirming method)
    (1) Description of first embodiment
    (2) First example of first embodiment (Particle fractionating treatment including performing particle confirming method of the present technology)
        (2-1) Trapping step
        (2-2) Correlating step
        (2-3) Discharging step
        (2-4) Particle moving step
        (2-5) ID information acquiring step
        (2-6) Confirming step
        (2-7) Example of particle confirming method in the case where adjacent wells have different pieces of ID information
        (2-8) Fractionating a plurality of particles
    (3) Second example of first embodiment (Particle confirming method using synthetic particle)
        (3-1A) Trapping step
        (3-2A) Correlating step
        (3-3A) Discharging step
        (3-4A) Particle moving step
        (3-5A) ID information acquiring step
        (3-6A) Confirming step
    (4) Example of particle
2. Second embodiment (Particle trapping chip)
    (1) Description of second embodiment
    (2) Example of fixation of label element to well
    (3) Example of coupling mode between label element and particle
    (4) Example of layout of label elements
    (5) First example of particle trapping chip
    (6) Second example of particle trapping chip
3. Third embodiment (Particle analyzing system)
    (1) Description of third embodiment
    (2) Example of third embodiment (Particle analyzing system)

1. First Embodiment (Particle Confirming Method)

(1) Description of First Embodiment

A particle confirming method of the present technology includes a correlating step of correlating ID information possessed by a particle trapped in a well in a particle trapping region with position information of the well, a discharging step of discharging the particle from the well, an ID information acquiring step of acquiring ID information of the particle after the discharging step, and a confirming step of confirming whether the particle has been trapped in the well possessing the position information, on the basis of the acquired ID information. In other words, in the particle confirming method of the present technology, the correlating step is conducted before the discharging step, and the ID information acquiring step and the confirming step are performed after the discharging step.

By the particle confirming method of the present technology, it is possible to confirm that an intended particle has been moved, after the particle trapped in the well is moved to the outside of the well. For example, by the particle confirming method of the present technology, it is possible to confirm, for example, whether the desired particle has been fractionated. Therefore, the particle confirming method of the present technology ensures that it is unnecessary to trace the desired particle by a camera, for confirming whether the desired particle has been fractionated. In addition, by the particle confirming method of the present technology, the position of the particle before the movement can be confirmed, after the particle trapped in the well is moved to the outside of the well. As a result, the well where the particle has been fractionated can be specified, and the particle yet to be fractionated and the particle having been fractionated can be correlated with each other.

In addition, by the particle confirming method of the present technology, the time and/or labor for confirming whether one desired particle has been fractionated can be reduced. The reduction of the time and/or labor is particularly conspicuous in an aspect of fractionating a plurality of desired particles. Therefore, the particle confirming method of the present technology is particularly suitable for an aspect of successively fractionating a plurality of desired particles.

Besides, by the particle confirming method of the present technology, the position of the particle before movement can be confirmed, after the particle trapped in the well is moved to the outside of the well. The confirmation also serves for, for example, correlating a cell component with a characteristic of a cell having the cell component. For example, a particle and a cell are made to coexist in a well, and the cell is dissolved to bind a nucleic acid derived from the cell to the particle. After the particle with the nucleic acid bound thereto is discharged from the well and recovered, the above-mentioned confirmation is conducted, whereby the nucleic acid derived from the cell and a characteristic of the cell can be correlated with each other.

Examples of the existing particle fractionating device include a flow cytometer. In a flow cytometer, a liquid in which cells are suspended is irradiated with laser light. A signal (for example, fluorescence and/or scattered light) generated by the irradiation is detected, and a cell fractionating operation is conducted, on the basis of the signal. The detection is performed within an extremely limited time, and information to be utilized for selection of the cell to be fractionated is limited to some extent.

The particle confirming method of the present technology includes a correlating step of correlating ID information possessed by the particle trapped in the well in a particle trapping region with position information of the well. After the correlating step, the particle is discharged from the well. In other words, the correlating step is conducted for the particle trapped in the well, and, thereafter, the particle is discharged. Therefore, much time can be consumed for selection of the particles to be fractionated, and, further, selection and fractionation of particles based on a more diversity of information can be performed.

The particle confirming method of the present technology may be performed in various particle fractionating devices in which a particle fractionating operation is conducted using a particle trapping region having at least one well. Examples of the various particle fractionating devices include a single cell analyzer in which a step of trapping a cell in a well is performed. As a result of analysis by the single cell analyzer, it may be required to fractionate the cell having been confirmed to have a desired characteristic. The particle confirming method of the present technology can respond to such a need, because the method makes it possible to confirm whether the desired particle has been fractionated.

The particle confirming method of the present technology may be performed when a particle fractionating treatment is carried out, for example. In other words, the present technology also provides a particle fractionating method including a step conducted in the particle confirming method (for example, the correlating step, the discharging step, the ID information acquiring step, the confirming step, etc.). An example of the particle fractionating method will be described in (2) below.

In addition, the particle confirming method of the present technology may be conducted, for example, in analysis of a cell component (particularly, a nucleic acid sequencing treatment), more particularly in sample preparation for analysis of a cell component. Thus, the present technology also provides a cell component analyzing method including a step conducted in the particle confirming method (for example, the correlating step, the discharging step, the ID information acquiring step, the confirming step, etc.). Besides, the present technology also provides a sample preparing method for cell component analysis including the step. An example of these methods will be described in (3) below.

(2) First Example of First Embodiment (Particle Fractionating Treatment Including Performing Particle Confirming Method of the Present Technology)

Figure 2A:
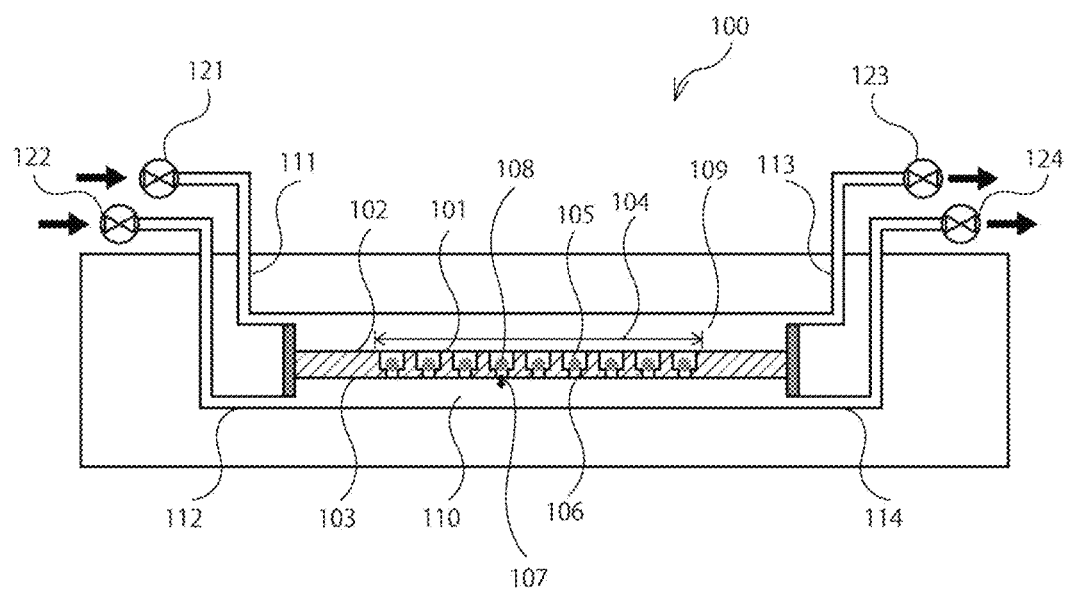
FIG. 2A is a schematic diagram depicting an example of a particle trapping chamber used in the particle confirming method according to the present technology.

An example of the particle confirming method of the present technology will be described below referring to FIG. 1, FIGS. 2A and B, and FIG. 3. FIG. 1 is an example of a flow of a particle fractionating treatment in which the particle confirming method of the present technology is conducted. FIGS. 2A and B illustrate an example of a particle trapping chamber used for the particle fractionating treatment. FIG. 3 illustrates schematic diagrams for explaining the particle fractionating treatment.

In step S101 of FIG. 1, a particle fractionating treatment in which the particle confirming method of the present technology is conducted is started. Prior to the start of the particle fractionating treatment, a particle trapping region having at least one well, and a liquid that contains or may possibly contain a particle to be fractionated may be prepared.

The particle trapping region may be, for example, a particle trapping region provided in a particle trapping chip to be described in "2. Second embodiment (Particle trapping chip)" below, for example. The description concerning the particle trapping chip and the description regarding a constituent element of the chip (for example, a particle trapping region or a well) apply also to the present embodiment.

Figure 2B:
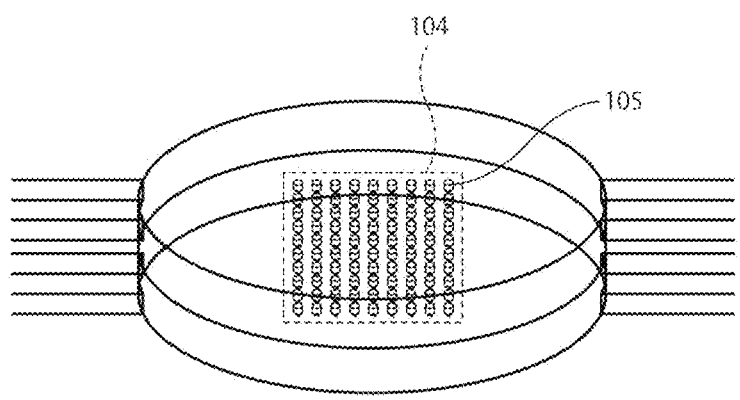
FIG. 2B is a schematic diagram depicting an example of the particle trapping chamber used in the particle confirming method according to the present technology.

The particle trapping chip may be provided in a particle trapping chamber. As the particle trapping chamber including the particle trapping chip, there may be prepared, for example, a particle trapping chamber depicted in FIGS. 2A and B. FIG. 2A is a diagram schematically depicting the inside of the particle trapping chamber. FIG. 2B is a schematic perspective view of the particle trapping chamber.

As illustrated in FIG. 2A, a particle trapping chamber 100 includes a particle trapping chip 101 that partitions the internal space of the particle trapping chamber 100 into two spaces. The particle trapping chip 101 has a particle trapping surface 102 and a surface 103 facing opposite to the particle trapping surface 102. The particle trapping chip 101 may be configured as a plate-shaped or sheet-shaped structure having these two surfaces. As depicted in FIGS. 2A and B, a particle trapping region 104 is provided at the particle trapping surface 102, and the particle trapping region 104 includes a plurality of wells 105. The well 105 has such a size as to be able to accommodate a particle in the inside of the well 105. As illustrated in FIG. 2A, each well 105 is provided with a hole 106 in a bottom portion of the each well 105. The hole 106 penetrates from the bottom portion of the well to the surface 103 on the opposite side. The hole 106 has such a size that the particle does not pass therethrough.

The particle trapping chip 101 (particularly, the region where the wells 105 are formed) may be formed from a material that is generally used in the technical field associated with microchannels, for example. Examples of the material include the followings: glasses, such as borosilicate glass and quartz glass; plastic resins, such as acrylic resin, cycloolefin polymer, and polystyrene; rubber materials; and silicone resins, such as PDMS.

For producing the particle trapping chip 101 (particularly, the region where the wells are formed), there may be used, for example, a 3D optical shaping method using an optical shaping printer or a high-definition 3D printer; a shaping method by shaping of a PDMS resin; a method of directly processing a glass by laser; or a method of processing an $SiO_2$ membrane by a semiconductor process. The apparatus for carrying out these methods may be selected, as required, by a person skilled in the art. As an apparatus used for the 3D optical shaping method, there may be mentioned, for example, an optical shaping printer of the ACCULAS (trademark) series. The resin used for 3D optical shaping may be selected, as required, by a person skilled in the art. The resin is, for example, a photo-curing resin composition containing one or more selected from among acrylic oligomers, acrylic monomers, epoxy oligomers, and epoxy monomers, and may, for example, be a UV-curing resin composition. The resin composition is cured by use of an optical shaping printer, whereby the particle trapping chip 101 may be formed. By these techniques, a particle trapping chip 101 having wells 105 and holes 106 having desired shapes can be produced.

Each of the wells 105 may have such a shape that one particle can be trapped. For example, the entrance of the well may be, for example, a circle, an ellipse, a polygon, for example, a triangle, a tetragon (e.g., a rectangle, a square, a parallelogram, a rhombus, etc.), a pentagon, a hexagon, etc. The entrance of the well in the present technology refers to an opening of the well in the particle trapping surface where the wells are provided. The shape of the entrance of the well may be designed, for example, such that the particle to be trapped can enter the well but the particles not to be trapped cannot enter the well.

The wells 105 may be regularly arranged on the particle trapping surface 102. The regular well arrangement makes it easier to specify the position of the well in which the desired particle is trapped, that is, makes it easier to acquire the position information which will be described below. As a result, it becomes easier, for example, to take out and/or observe the particle trapped by the well. For example, the wells may be arranged at regular intervals in a row or a plurality of rows on the particle trapping surface, or the wells may be arranged at regular intervals in a grid pattern on the particle trapping surface. The interval may be selected, as required, by a person skilled in the art according, for example, to the number of particles applied or the number of particles to be trapped. The interval may be, for example, 20 to 300 μm, preferably 30 to 250 μm, more preferably 40 to 200 μm, and further preferably 50 to 150 μm. In the case where the wells are arranged, for example, in a grid pattern, the wells may be arranged at the above-exemplified intervals in an X direction and a Y direction on the particle trapping surface.

The material of other part of the particle trapping chamber 100 (particularly, the material forming a wall surface defining an internal space of the chamber 100 and the material forming a wall surface of a channel connected to the internal space of the chamber 100) may be selected, as required, by a person skilled in the art. For example, in the case where the particle is a cell, the material is preferably a material that is not toxic to the cell. In addition, in the case where fluorescence observation of the trapped particle is conducted, it is preferable to use a material that does not emit self-fluorescence exceeding an allowable range. Besides, it is preferable to use a material that enables observation of a particle trapped by a particle in the well. For observation of the particle, for example, at least a part of the chamber, particularly an upper surface of the particle trapping chamber 100 (that is, a ceiling part of a particle trapping space 109) may be formed from a transparent material.

As a material of the other part of the particle trapping chamber 100, there may be used, for example, a material generally used in the technical field of microchannels. Examples of the material include the followings: glasses, such as borosilicate glass or quartz glass; plastic resins, such as acrylic resins, cycloolefin polymer, and polystyrene; or rubber materials, such as PDMS. In the case where the particle trapping chamber of the present technology is configured by a plurality of materials, the plurality of materials may be the same material, or may be different materials. For example, by stacking a plurality of plate-shaped materials preliminarily formed with a hole or holes for forming a chamber internal space or a channel space, the particle trapping chamber of the present technology may be formed.

The inside of the particle trapping chamber 100 is partitioned into two spaces by the particle trapping chip 101. The space on the side on which the well 105 is opened is referred to as a particle trapping space 109, and the other space is referred to as an opposite-side space 110.

The particle trapping chamber 100 is disposed such that gravity acts on the particle 108 in the direction of an arrow 107.

As illustrated in FIG. 2A, the particle trapping chamber 100 includes a first fluid supply channel section 111, a second fluid supply channel section 112, a first fluid discharge channel section 113, and a second fluid discharge channel section 114. The first fluid supply channel section 111 and the first fluid discharge channel section 113 are connected to the particle trapping space 109. The second fluid supply channel section 112 and the second fluid discharge channel section 114 are connected to the opposite-side space 110.

The first fluid supply channel section 111, the second fluid supply channel section 112, the first fluid discharge channel section 113, and the second fluid discharge channel section 114 are provided with valves 121, 122, 123, and 124, respectively.

Pumps (not illustrated) are respectively connected to the four channel sections. With the pumps driven, a fluid can be supplied into the particle trapping chamber 100 through these four channel sections, or a fluid can be sucked from inside the particle trapping chamber 100 through these four channel sections. These four valves and four pumps can be controlled independently from one another.

Note that FIG. 2A is a schematic diagram of an example of a state in which the particles are trapped in the wells 105, and the particles may not be present in the wells 105 before a particle trapping treatment.

An enlarged view of the particle trapping region 104 is depicted in FIG. 3(a). As depicted in FIG. 3(a), plural wells 105 are provided on a surface of the particle trapping region 104. The plural wells 105 are preferably arranged at predetermined intervals. With the plural wells 105 arranged at the predetermined intervals, position information of the wells in which the particles are to be trapped can be easily acquired in the correlating step which will be described later. Note that in FIG. 3, the holes 106 in the wells 105 are omitted.

The plural wells 105 may be arranged in a grid pattern, for example, as depicted in FIG. 3(a). With the wells 105 arranged in a grid pattern, position information associated with the wells can be easily acquired.

The respective sizes of the plural wells 105 may be selected, as required, by a person skilled in the art according to the sizes of the particles to be fractionated. The well 105 may have a size such as to be able to accommodate, for example, at least one particle to be fractionated, or may have a size such as to be able to accommodate preferably one to five particles to be fractionated, more preferably one to three particles, further preferably one or two particles, and particularly preferably one particle to be fractionated.

The fluid that contains or may contain the particles to be fractionated (herein referred to also as "desired particles") may be, for example, a fluid containing a plurality of kinds of cells. The fluid may contain other particles than the desired particles.

(2-1) Trapping Step

In step S102, a trapping step is conducted in which the particles are trapped in the wells in the particle trapping region. In the trapping step, a particle trapping treatment may be performed such that at least one well in which one particle has been trapped is present in the particle trapping region.

As a result of the trapping step, the well in which two or more particles have been trapped may be present. The well in which two or more particles have been trapped is excluded from the object of fractionation in the following correlating step.

The particle trapping treatment may be performed in such a manner that the particle falls to enter the well or that the particle rises to enter the well. The fall of the particle may be, for example, sedimentation of the particle due to gravity, and the rise of the particle may be, for example, a movement of the particle due to a flow generated by suction.

According to one embodiment of the present technology, in the trapping step, the particle may be trapped in the well through a linker fixed to the well in the particle trapping region. With the linker utilized, the particle can be trapped more securely into the well. As the linker, a linker as described in "2. Second embodiment (Particle trapping chip)" below may be used, and the description applies also to the present embodiment.

In step S102, a cell-containing liquid is introduced into the particle trapping space 109 from the first fluid supply channel section 111 depicted in FIGS. 2A and B, for example. As a result, the cells 108 are sedimented in the particle trapping space 109 to enter the wells 105, respectively, and the cells 108 are trapped in the wells 105 as depicted in FIG. 3(b), for example.

For example, the cells trapped in the wells may have different fluorescence labels. That the cells have the different fluorescence labels is represented by that the cells have different patterns, in FIG. 3(b).

Simultaneously with the introduction, for example, suction through the second fluid discharge channel section 114 may be conducted. In addition to the suction through the second fluid discharge channel section 114, suction through the second fluid supply channel section 112 may be performed. By such suction, the particles 108 can be trapped into the wells 105 more efficiently. In addition, by the suction, the trapped particles 108 are restrained from going out of the wells 105.

The trapping step in step S102 may include a labeling step of labeling the particle trapped in the well to impart ID information to the particle. In the labeling step, for example, with the particle trapped in the well, the particle may be labeled with a label element present in the well. In the present technology, the label element may be a substance for labeling the particle. For example, in the labeling step, the particle may be labeled with fluorescence, a color, an electric charge, a magnetic charge, or a radical, thereby imparting ID information to the particle.

With the particle labeled with the label element, ID information to be utilized in steps after the trapping step which will be described below (for example, the correlating step, the ID information acquiring step, the confirming step, etc.) can be imparted to the particle. With the ID information imparted, the steps after the trapping step which will be described below can be performed more easily.

According to one embodiment of the present technology, in the labeling step, adjacent wells in the particle trapping region may have different label elements, and the particles trapped in the adjacent wells may be labeled with the different label elements. With the adjacent wells having the different label elements, it becomes easy, for example, to confirm whether the particle having acquired ID information in the ID information acquiring step described later is the particle having been trapped in the well having position information correlated in the correlating step.

The particle trapping region in which the adjacent wells have different label elements will be described below referring to FIGS. 4 and 5.

Figure 4:
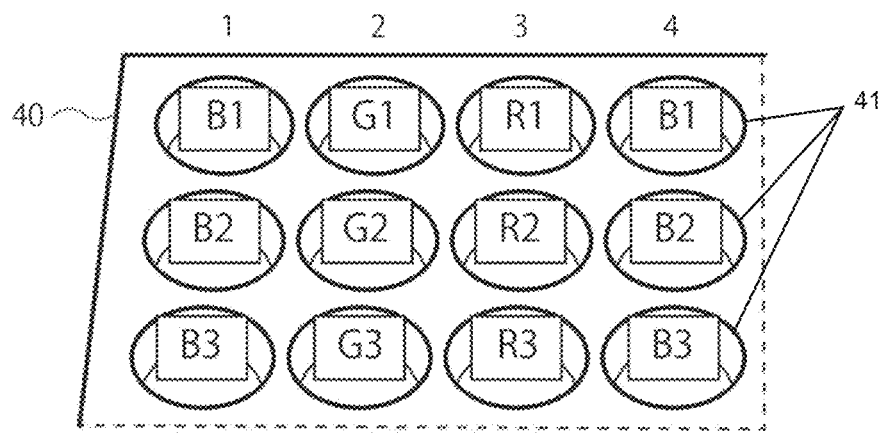
FIG. 4 is a schematic diagram of an example of a particle trapping region used in the particle confirming method according to the present technology.

FIG. 4 is a diagram schematically depicting an example of the particle trapping region. In the particle trapping region illustrated in FIG. 4, fluorescent dyes of nine colors are used as label elements.

Plural wells 41 are arranged in a grid pattern in a particle trapping region 40 in FIG. 4. In the particle trapping region 40, the wells in column 1 have any one of three kinds of blue fluorescent dyes B1, B2, and B3 having mutually different wavelengths as a label element. Each of the wells in column 1 has any one of the blue fluorescent dyes B1, B2, and B3 as a label element in such a manner that B1, B2, and B3 are aligned in this order. The wells in column 2 have any one of three kinds of green fluorescent dyes G1, G2, and G3 having mutually different wavelengths as a label element. Each of the wells in column 2 has any one of the green fluorescent dyes G1, G2, and G3 as a label element in such a manner that G1, G2, and G3 are aligned in this order. The wells in column 3 have any one of three kinds of red fluorescent dyes R1, R2, and R3 having mutually different wavelengths as a label element. Each of the wells in column 3 has any one of the red fluorescent dyes R1, R2, and R3 as a label element in such a manner that R1, R2, and R3 are aligned in this order. In column 4 and the subsequent columns, similarly, a column formed by wells having any one of three kinds of blue fluorescent dyes, a column formed by wells having any one of three kinds of green fluorescent dyes, and a column formed by wells having any one of three kinds of red fluorescent dyes are aligned in this order.

With the fluorescent dye thus disposed in each well, a particle trapping region in which the adjacent wells have different label elements is formed. As a result, the particles trapped in the adjacent wells are labeled with different label elements.

Figure 5:
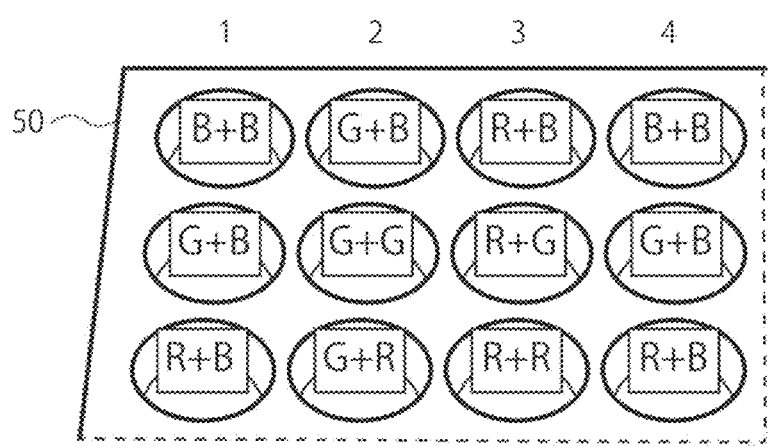
FIG. 5 is a schematic diagram of another example of the particle trapping region used in the particle confirming method according to the present technology.

FIG. 5 is a diagram schematically depicting another example of the particle trapping region. In the particle trapping region illustrated in FIG. 5, combinations of two of fluorescent dyes of three colors are used as label elements.

Plural wells are arranged in a grid pattern in a particle trapping region 50 in FIG. 5. In the particle trapping region 50, the wells in column 1 have any one of a combination of a blue fluorescent dye B and a blue fluorescent dye B, a combination of a blue fluorescent dye B and a green fluorescent dye G, and a combination of a blue fluorescent dye B and a red fluorescent dye R. Each of the wells in column 1 has any one of these combinations as a label element in such a manner that these combinations are aligned in this order. The wells in column 2 have any one of a combination of G and B, a combination of G and G, and a combination of G and R. Each of the wells in column 1 has any one of these combinations as a label element in such a manner that these combinations are aligned in this order. The wells in column 3 have any one of a combination of R and B, a combination of R and G, and a combination of R and R. Each of the wells in column 1 has any one of these combinations as a label element in such a manner that these combinations are aligned in this order.

With two kinds of fluorescent dyes thus arranged in each well, a particle trapping region in which the adjacent wells have different label elements is formed. As a result, the particles trapped in the adjacent wells are labeled with different label elements.

According to one embodiment of the present technology, in the labeling step, the wells in the particle trapping region may be arranged such as to form a plurality of rows or columns. Further, the adjacent two rows or columns constituting the plurality of rows or columns may have mutually different label elements, and the particles trapped in the wells in the adjacent rows or columns may be labeled with different label elements. With the adjacent two rows or columns having mutually different label elements, it becomes easy, for example, to confirm whether the particles having acquired ID information in the ID information acquiring step described later are the particles having been trapped in the wells having position information correlated in the correlating step.

A particle trapping region in which the adjacent two rows or columns have mutually different label elements will be described below referring to FIGS. 6 and 7.

Figure 6:
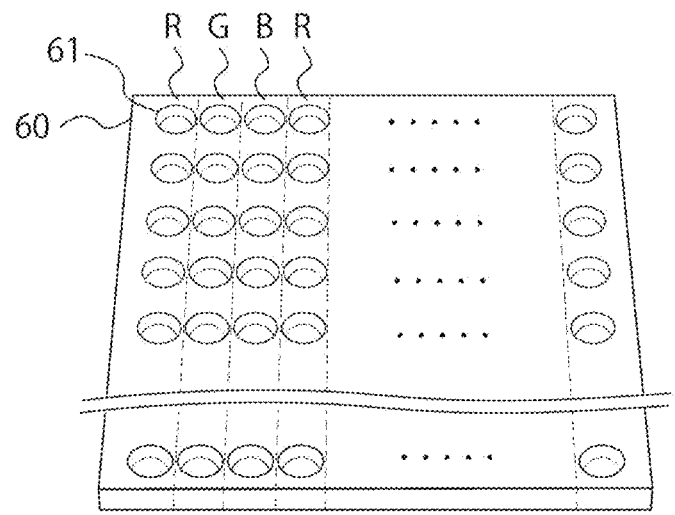
FIG. 6 is a schematic diagram of still another example of the particle trapping region used in the particle confirming method according to the present technology.

FIG. 6 is a diagram schematically depicting still another example of the particle trapping region. In the particle trapping region illustrated in FIG. 6, any one of fluorescent dyes of three colors is used as a label element.

Plural wells 61 are arranged in a grid pattern in a particle trapping region 60 in FIG. 6. In the particle trapping region 60, a column in which wells having red fluorescent dyes R are aligned, a column in which wells having green fluorescent dyes G are aligned, and a column in which wells having blue fluorescent dyes B are aligned are aligned in this order. With any one of the three kinds of fluorescent dyes thus disposed in each well, a particle trapping region in which the adjacent columns have mutually different label elements is formed. As a result, the particles trapped in the adjacent columns are labeled with different label elements.

Figure 7:
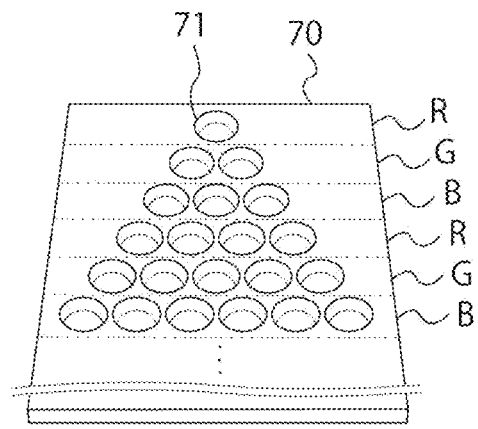
FIG. 7 is a schematic diagram of yet another example of the particle trapping region used in the particle confirming method according to the present technology.

FIG. 7 is a diagram schematically depicting yet another example of the particle trapping region. In the particle trapping region illustrated in FIG. 7, any one of fluorescent dyes of three colors is used as a label element.

Plural wells 71 are arranged such as to form a triangle in a particle trapping region 70 in FIG. 7. In the particle trapping region 70, a row in which wells having red fluorescent dyes R are aligned, a row in which wells having green fluorescent dyes G are aligned, and a row in which wells having blue fluorescent dyes B are aligned are aligned in this order. With any one of the three kinds of fluorescent dyes disposed in the wells in each row, a particle trapping region in which the adjacent rows have mutually different label elements is formed. As a result, the particles trapped in the adjacent rows are labeled with different label elements.

According to another embodiment of the present technology, in the labeling step, the particle trapping region may be divided into a plurality of fields, and the wells may include label elements for specifying the field in which the well is disposed.

A particle trapping region divided into a plurality of fields will be described below referring to FIG. 8.

Figure 8:
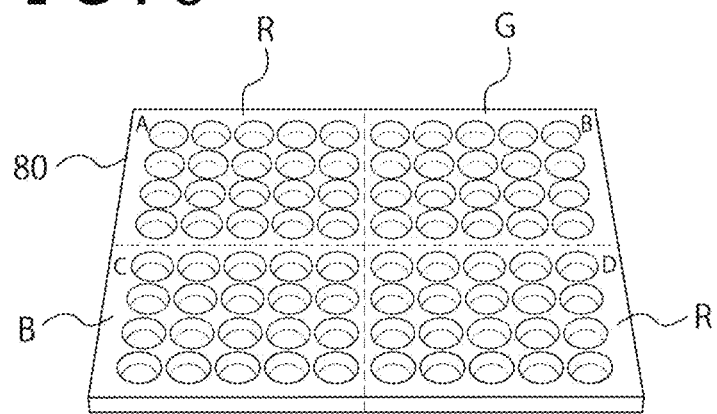
FIG. 8 is a schematic diagram of further example of the particle trapping region used in the particle confirming method according to the present technology.

FIG. 8 is a diagram schematically depicting further example of the particle trapping region. The particle trapping region illustrated in FIG. 8 is divided into four regions.

A particle trapping region 80 of FIG. 8 is divided into four fields A to D. A red fluorescent dye R is disposed in every one of the wells belonging to the fields A and D. A green fluorescent dye G is disposed in every one of the wells belonging to the field B. A blue fluorescent dye B is disposed in every one of the wells belonging to the field C. As a result, the particle trapped in any well in the field A is labeled with the red fluorescent dye R. In a case where, after the particle is discharged from the well and moved into other container, the fluorescence of the particle in the container is due to the red fluorescent dye R, it is confirmed that the particle has been trapped in the well in the field A.

(2-2) Correlating Step

In step S103, a correlating step is conducted in which ID information possessed by the particle trapped in the well in the particle trapping region is correlated with position information of the well. In other words, in the correlating step, the particle having the ID information and the position of the well in which the particle is trapped are tied up. The ID information and the position information correlated with each other are used in a confirming step which will be described below.

The correlating step may be performed mechanically, or may be conducted by the user who performs a particle fractionating operation by utilizing the particle trapping region.

In the case where the correlating step is conducted mechanically, the correlating step may be performed, for example, by a system for performing correlation. The system may be, for example, a particle analyzing system described below. The particle analyzing system may include, for example, a particle trapping chamber, a microscope, an imaging device, and a particle confirming section. The particle analyzing system will be described in "3. Third embodiment (Particle analyzing system)" below.

In the case where the correlating step is conducted by the user, the user may select the particle having the ID information in a visual field under microscope observation, for example, and may correlate the ID information of the particle with the position information of the well in which the particle is trapped. In the correlating step, the ID information and the position information may be recorded or stored by the user.

In the present technology, the "ID information" may be information used for discriminating a particle from other particles, or may be information used for identifying a particle. The discrimination or the identification may be conducted, on the basis of the kind or characteristics of the particle, for example. More specifically, the ID information may be information based on the fluorescence, color, electric charge, magnetic charge, or radical of the particle trapped in the well, or may be information associated with the form or size of the particle trapped in the well. As the ID information, a combination of two or more of these pieces of information may be used.

In the present technology, the "position information" may be information associated with the position of the well in which the particle is trapped. The position information may be information regarding the position of the well in which the particle is trapped in one visual field under microscope observation, for example, or may be information associated with the position of the particle in one visual field under microscope observation. The position information may be information regarding the position of the well in which the particle is trapped in the particle trapping region, for example, or may be information associated with the position of the particle in the particle trapping region.

The position information may be position information in a coordinate system, or may be position information in a non-coordinate system.

The position information in a coordinate system may be, for example, position information represented by a one-dimensional or two-dimensional coordinate system, more particularly may be position information represented by a rectangular coordinate system. The coordinate axes and the origin may be set, as required, by a person skilled in the art or by a particle analyzing system.

It is sufficient that the position information in the non-coordinate system is information which can be utilized for specifying the position in which the particle is trapped in one visual field under microscope observation, for example. For example, in the case where wells forms a plurality of columns and rows in the one visual field, at which numbered column from the left or the right in the one visual field the well exists or at which numbered row from the upper side or the lower side in the one visual field the well exists may be used as the position information in the non-coordinate system. The position information in the non-coordinate system may be relative position information. The relative position information may be, for example, position information based on ID information of the particle trapped in the well in the surroundings of the well in which the particle of concern is trapped. For example, that a well in which a particle having certain ID information is trapped is surrounded by wells in which a particle having different ID information from the certain ID information is trapped or in which a particle not having the certain ID information is trapped may be used as position information of the well in which the particle having the certain ID information is trapped. Alternatively, that a well in which a particle having certain ID information is trapped is located near a well in which a particle having different ID information from the certain ID information is trapped or in which a particle not having the certain ID information is trapped may be used as position information of the well in which the particle having the certain ID information is trapped.

In the correlating step, for example, as illustrated in FIG. 3(c), position information of a well 105 in which a cell 108 is trapped is correlated with ID information of the cell 108.

In the case where the position information of the well 105 is represented by a two-dimensional rectangular coordinate system, for example, position information of (X, Y)=(6, 4) may be acquired. Further, ID information of the cell 108 may be acquired, and, for example, ID information that the cell 108 has green fluorescence may be acquired. The position information and the ID information are correlated with each other, and that the particle trapped in the well having the position information of (X, Y)=(6, 4) has green fluorescence is recorded mechanically (for example, by a control section of a particle analyzing system) or may be recorded or stored by the user.

According to one embodiment of the present technology, the correlating step may include an image acquiring step of acquiring an image of the particle trapping region. ID information of the particle trapped in the well and position information of the well may be acquired from the image, and then the ID information and the position information may be correlated with each other. The ID information acquired from the image may be, for example, fluorescence or color of the particle or the size or shape of the particle.

In the image acquiring step, the ID information and/or the position information may be obtainable by, for example, acquiring image data by an imaging device such as a camera and processing the image data.

(2-3) Discharging Step

In step S104, a discharging step is conducted in which a particle trapped in a well is discharged from the well. For the discharging, for example, the well in which the particle is trapped may be irradiated with laser light or ultrasonic wave. By the irradiation with the laser light or ultrasonic wave, a bubble is generated, whereby the desired particle can be discharged from the well. For example, by utilizing laser having an oscillation wavelength in the vicinity of light absorption wavelength of water (for example, holmium YAG (Ho: YAG) laser) and giving huge energy to the water in a short time, a bubble can be generated.

Alternatively, for the discharging, by use of a particle operating device such as, for example, a micromanipulator or a micropipette, the desired particle may be discharged from the well.

Alternatively, for the discharging, a sheet for sealing the wells in the particle trapping region may be used. After trapping of the particle, the wells in the particle trapping region may be sealed with the sheet. Next, a hole is opened at only the sheet part covering the well in which the desired particle is trapped. A flow for discharging the desired particle from the well is formed in the particle trapping chamber. By this, the desired particle can be discharged from the well, while keeping the other particles trapped in the wells.

For enabling opening of the hole, the sheet may be formed from, for example, a ray (for example, IR ray)-absorbing material. By irradiating the sheet part with rays (for example, IR rays), the hole is opened.

The discharging step may include a treatment step of performing a step for enabling a particle trapped in a well to be discharged from the well. For example, in the case where a particle is fixed to a well by a linker in the trapping step, the linker may be cut in the treatment step to enable the particle to be discharged from the well. The linker cutting treatment may be selected, as required, by a person skilled in the art according to the kind of the linker. A specific example of the linker will be described in "2." below.

In a preferred embodiment of the present technology, the treatment step may include a light irradiation step in which the linker fixed to the well is irradiated with light to cut the linker. For example, in the case where the linker is to be cut by irradiation with UV rays, the cutting treatment may be UV ray irradiation.

According to one embodiment of the present technology, in the discharging step, plural particles having ID information may be discharged successively. For example, in the discharging step, 2 to 100 particles, particularly 2 to 50 particles, more particularly 2 to 30 particles which have ID information may be discharged successively. As a result, the order of pieces of ID information of the plural particles discharged successively can be referred to in the confirming step described later.

For instance, the discharging step may be conducted in such a manner that particles having the same ID information are not discharged successively. In other words, the discharging step may be performed in such a manner that the two particles discharged successively have different pieces of ID information. For example, a particle having red fluorescence, a particle having blue fluorescence, and then a particle having red fluorescence may be discharged in this order. The order of pieces of ID information of such particles discharged may be compared, in the confirming step described below, with, for example, the order of pieces of ID information acquired in the ID information acquiring step. In such a way, in the discharging step, two or more particles discharged successively may have different pieces of ID information.

Alternatively, the discharging step may be performed in such a manner that particles having the same ID information are discharged successively. For example, three particles having red fluorescence may be discharged successively. That the particle having the same ID information are discharged successively may also be compared, in the confirming step described below, with the order of pieces of ID information acquired in the ID information acquiring step.

For example, in the discharging step, the discharge may be temporarily stopped after a predetermined number of particles are discharged successively. Then, after the temporary stop of the discharge, successive discharge of the particles may be restarted again. By this, the temporary stop of the discharge may be utilized, for example, as a sign for change of the container or well into which the particles are to be recovered.

Alternatively, in the discharging step, a particle to be a mark may be discharged after a predetermined number of particles are discharged successively. The particle to be a mark may be utilized, for example, as a sign for change of the container or well into which the particles are to be recovered. The particle to be a mark may be, for example, a particle having predetermined ID information. The predetermined ID information may be set by a person skilled in the art, and may preferably be different ID information from the ID information for specifying the particle to be fractionated.

In the discharging step, the cell 108 trapped in the well 105 is discharged from the well 105, as depicted in FIG. 3(d), for example. For the discharging, for example, the well 105 is irradiated with laser light 30. A bubble is generated in the well by the irradiation, and the cell 108 is discharged from the well 105 by the bubble.

In addition, in the case where the cell 108 is fixed to the well through a linker, a linker cutting treatment may be conducted before the discharge by, for example, irradiation with UV rays.

(2-4) Particle Moving Step

In step S105, a particle moving step may be conducted in which the particle discharged from the well in the discharging step is moved from the particle trapping region to other region. The other region may be the container inside of a particle recovering container, or may be a well of a particle recovering plate. In such a way, the desired particle may be fractionated into the container or the plate.

According to one embodiment of the present technology, in the particle moving step, the particle discharged from the well is made to pass through a channel. The channel may be one for guiding the particle to the container or plate for particle recovery, for example. During or after the passage through the channel, the ID information acquiring step and/or the confirming step described later may be conducted.

The moving distance of the particle in the particle moving step may be, for example, a distance that is not included within one visual field of the microscope used in the correlating step, or may be a distance that is not included within an imaging range of the imaging device used in the correlating step. In the case of moving the desired particle over a distance exceeding the one visual field or the imaging range, it is necessary, for confirming that the desired particle is fractionated, to trace the desired particle by movement of the visual field or by movement of the imaging device. The particle fractionating method of the present technology makes it possible to confirm whether the desired particle has been fractionated, without tracing the desired particle, by performing the ID information acquiring step and the confirming step which will be described below.

The particle discharged from the well in the discharging step may be guided to a channel connected on a fluid basis to a space in which the particle trapping region is disposed, by a flow of a fluid formed in the periphery of the particle trapping region, and the particle may be recovered into the container or onto the plate for particle recovery through the channel. Alternatively, the particle discharged from the well in the discharging step may be moved in a channel connected to a micropipette and recovered into the container or onto the plate for particle recovery connected to the channel, or may be moved into the container or onto the plate for particle recovery by a micromanipulator.

In addition, in the container or on the plate, further particle analysis may be performed. For example, in the case where the particle is a cell, analysis or cultivation of the cell may be conducted in the container or on the plate.

For instance, in the case of performing the particle confirming method according to the present technology by use of the particle trapping chamber 100 depicted in FIGS. 2A and B, in the particle moving step, the cell 108 is moved through the first fluid discharge channel section 113 to the outside of the chamber 100. For the movement, for example, suction by a pump (not illustrated) connected to the first fluid discharge channel section 113 through the valve 123 may be performed. By the suction, the cell 108 in the particle trapping space 109 is passed through the first fluid discharge channel section 113 and discharged to the outside of the chamber 100.

The first fluid discharge channel section 113 is connected to a particle recovering channel 130 depicted in FIG. 3(e), for example, and the particle recovering channel 130 is configured such that the particle can be discharged into any one of wells of a 96-well plate 131, for example. After passed through the particle recovering channel 130, the cell 108 is recovered into any one of the wells of the 96-well plate 131.

(2-5) ID Information Acquiring Step

In step S106, an ID information acquiring step is conducted in which ID information of a particle is acquired after the discharging step. The ID information acquiring step is performed after the discharging step. In other words, in the particle fractionating method of the present technology, the ID information of the particle is acquired respectively in two different steps, that is, in the correlating step before the discharging step and in the ID information acquiring step after the discharging step. In the former step, the particle is in the state of being trapped in the well. The latter step is conducted after the discharging step, in other words, the particle is present outside the well in the latter step. By thus acquiring the ID information of the particle trapped in the well and the ID information of the particle having been discharged from the well, it is possible to confirm whether the desired particle has been fractionated. For example, the ID information acquiring step may be conducted during the particle moving step described in "(2-3) Discharging step" above, or may be performed in the case where the particle is present in the container or on the plate for particle recovery.

In the case where the particle confirming method of the present technology further includes a particle moving step in which the particle discharged from the well in the discharging step is passed through a channel, the ID information may be acquired from the particle to be passed through the channel or the particle having passed through the channel, in the ID information acquiring step. Specifically, the ID information acquiring step may be conducted in any time during the process in which the particle discharged from the well is moved through the channel for guiding to the particle recovering container, or may be conducted after the particle is passed through the channel and recovered into the particle recovering container.

In the ID information acquiring step, the ID information of the particle recovered into one well of the 96 well plate 131 may be acquired, for example, by an ID information acquiring device such as a microscope 132, as depicted in FIG. 3(f), for example.

Alternatively, in the ID information acquiring step, ID information may be acquired from the particle passing through a channel 130 depicted in FIG. 3(e). For example, fluorescence and/or scattered light generated by irradiation of the particle passing through the channel 130 with light may be acquired as ID information. For acquiring the ID information in such a way, for example, a light detecting technique utilized in a flow cytometer or a cell sorter may be applied.

(2-6) Confirming Step

In step S107, a confirming step is conducted in which whether the particle has been trapped in the well having the position information is confirmed, on the basis of the acquired ID information. For example, in the confirming step, the position of the well in which the particle has been trapped may be confirmed, on the basis of the ID information acquired in the ID information acquiring step.

The confirming step may be performed mechanically, or may be conducted by the user who performs the particle fractionating operation by utilizing the particle trapping region.

In the case of mechanically performing the confirming step, the confirming step may be carried out, for example, by a particle analyzing system to be described in "3. Third embodiment (Particle analyzing system)" below, particularly by a confirming section and/or a control section included in the system.

In the case of performing the confirming step by the user, the user may confirm the position of the well in which the particle has been trapped, on the basis of the ID information of the particle recovered into the particle recovering container, for example.

According to one embodiment of the present technology, in the confirming step, the order of discharge of a plurality of particles having ID information may be referred to. For example, when the order of pieces of ID information of the particles discharged in the discharging step and the order of pieces of ID information of the particles acquired in the ID information acquiring step, in regard to a group of a predetermined number of successive particles, are different from each other, the group of particles may be disposed of.

For example, a case where a particle having red fluorescence, a particle having blue fluorescence, and a particle having red fluorescence are discharged in this order in the discharging step, and pieces of ID information of red, red, and blue are acquired in the ID information acquiring step is assumed. In the confirming step, the order of discharge in the discharging step and the order of the fluorescence acquired in the ID information acquiring step are compared with each other, and it is confirmed that both orders are different from each other. As a result, it may be confirmed in the confirming step that the desired particles have not been acquired.

In addition, a case where three particles having red fluorescence are discharged successively in the discharging step and pieces of ID information of red, blue, and red are acquired in the ID information acquiring step is also assumed. In the confirming step, the order of discharge in the discharging step and the order of fluorescence acquired in the ID information step are compared with each other, and it is confirmed that both orders are different from each other. As a result, it may be confirmed in the confirming step that the desired particles have not been acquired.

In the case where it is confirmed that the group of particles acquired is not the desired particles, the acquired particles may be disposed of.

According to one embodiment of the present technology, in the confirming step, the ID information acquired in the ID information acquiring step and the ID information acquired in the correlating step may be compared with each other.

In the case where these pieces of ID information coincide with each other as a result of the comparison, it may be confirmed that the particle of which the ID information has been acquired in the ID information acquiring step and the particle which is an object of correlation in the correlating step are the same. Since the ID information and the position information regarding the particle which is the object of correlation in the correlating step are correlated with each other, it may be confirmed that the particle of which the ID information is acquired in the ID information acquiring step has been trapped in the well having the position information correlated in the correlating step.

In the case where as a result of the comparison, these pieces of ID information are not coincident with each other, it is confirmed that the particle of which the ID information is acquired in the ID information acquiring step is not the same as the particle which is an object of correlation in the correlating step; further, it may be confirmed that the particle of which the ID information is acquired in the ID information acquiring step has not been trapped in the well having the position information correlated in the correlating step.

In this way, in the confirming step, it may be confirmed whether the particle to be fractionated has been fractionated.

In the case where it is confirmed in the confirming step that the particle to be fractionated has not been fractionated, the particles recovered into the wells of the 96-well plate 131 may be disposed of.

Alternatively, in the case where it is confirmed in the confirming step that the particle to be fractionated has not been fractionated, the particles may not be recovered into the wells of the 96-well plate 131, and the particles may be disposed of. For disposing of the particles in such a way, it is preferable that the ID information acquiring step and the confirming step are conducted during when the particles are flowing in the channel 130.

In step S108, the particle fractionating treatment including the particle confirming method according to the present technology is finished.

(2-7) Example of Particle Confirming Method in the Case where Adjacent Wells have Different Pieces of ID Information A more specific work of performing the particle confirming method according to the present technology by use of the particle trapping region depicted in FIG. 4 will be described below.

For example, it is assumed to confirm whether a particle trapped in a well having a green fluorescent dye G2 in FIG. 4 has been fractionated.

First, in the trapping step, the particle in a well having the green fluorescent dye G2 is trapped. By the trapping, the green fluorescent dye G2 is transferred to the particle. Thereafter, in the correlating step, the position information of the particle and ID information (fluorescence information) of the green fluorescent dye G2 possessed by the particle are correlated with each other. After the correlating step, a discharging step is conducted, whereby the particle is discharged from the well. After the discharging step, the particle is moved to a container or plate for particle recovery. During or after the movement, an ID information acquiring step is conducted, whereby the fluorescence information of the particle is acquired as ID information. In the confirming step, on the basis of the ID information acquired in the ID information acquiring step, it is confirmed whether the particle recovered into the particle recovering container or onto the plate is the particle having been trapped in the well. For instance, in the case where the ID information acquired in the ID information acquiring step is fluorescence information other than G2 (for example, in the case where the acquired ID information is G1, R2 or the like), it is confirmed that the particle trapped in the well having the green fluorescent dye G2 has not been discharged. In addition, in the case where the ID information acquired in the ID information acquiring step is the fluorescence information of G2, it is confirmed that the particle having been trapped in the above-mentioned well has been fractionated.

The work as described above may be carried out also by use of the particle trapping regions depicted in FIGS. 5 to 8, for example. In such a way, the particle confirming method of the present technology can be performed using various particle trapping regions.

(2-8) Fractionating a Plurality of Particles

The particle fractionating treatment as above is particularly suitable in the case of fractionating a plurality of particles, for example. The details of the particle fractionating treatment for fractionating plural desired particles will be described below.

In the case of fractionating plural desired particles, plural particles having ID information are discharged successively, in the discharging step, for example. The plural particles may be particles that have the same ID information, or may be particles that have mutually different pieces of ID information.

In the case where the particles having the same ID information are discharged successively, when the presence of a particle having different ID information from the ID information is confirmed in the confirming step, it is seen that the plural particles discharged successively include a particle or particles other than the desired particle. This serves for selecting the recovery of the plural particles discharged successively or disposal of the plural particles.

In the case where particles having different pieces of ID information are discharged successively, it is preferable that the pieces of ID information possessed by the plural particles to be discharged and the order of discharge of the plural particles are determined prior to the discharging step (for example, during or after the correlating step). As a result, in the case where, for example, the ID information acquiring step is conducted regarding the particles passing through a channel in the particle moving step, it may be confirmed in the confirming step whether the desired particles have been recovered according to the order of discharge, by comparing the pieces of ID information of the particles passing through the channel and the order of discharge. In such a way, the order of discharge of the plural particles may be referred to in the confirming step.

In the case of fractionating a plurality of desired particles, for example, after a predetermined number of particles are discharged successively in the discharging step, the discharge may be stopped temporarily, or a particle to be a mark may be discharged. The stopping of the primary particle discharge or the discharge of the particle to be a mark may be utilized, for example, for confirming the number of particles recovered, or may be utilized as a sign for switching the container or wells into which the particles are recovered.

(3) Second Example of First Embodiment (Particle Confirming Method Using Synthetic Particle)

According to one embodiment of the present technology, the particle trapped in the well in the correlating step may have two or more different pieces of ID information. For example, the ID information correlated in the correlating step and the ID information acquired in the ID information acquiring step may be different from each other. Using these two different pieces of ID information, the position of the well in which the particle has been trapped may be confirmed in the confirming step.

The two or more different pieces of ID information may be selected, as required, according to, for example, means (for example, a device) for acquiring ID information in the correlating step and means (for example, a device) for acquiring ID information in the ID information acquiring step.

For instance, in the case where a fluorescence detector is used for acquiring ID information in the correlating step, the ID information acquired in the correlating step may be fluorescence, and, in the case where a sequencer (a sequencer for nucleic acid sequence or amino acid sequence) is used for acquiring ID information in the ID information acquiring step, the ID information acquired in the ID information acquiring step may be sequence information (nucleic acid sequence or amino acid sequence).

A more specific example of the present embodiment will be described below.

First, an example of a particle having two or more different pieces of ID information used in the present embodiment will be described referring to FIG. 9.

A particle 90 depicted in FIG. 9 includes a particle main body 91 and a nucleic acid 92 (for example, DNA, RNA or the like) bound to the particle main body 91.

The particle main body 91 may be, for example, a synthetic particle. The surface of the synthetic particle may have an inorganic layer (inorganic metal layer) or an organic layer. The particle main body 91 may have a fluorescent label element as ID information, on the surface of the particle main body 91, for example. The label element may be, for example, a quantum dot. Particularly, a combination of quantum dots may be used as ID information. For example, as depicted in (a), (b), and (c) of FIG. 10, a variety of pieces of ID information can be generated by changing variously the numbers of quantum dots having red fluorescence, quantum dots having green fluorescence, and quantum dots having blue fluorescence. By adopting the quantum dots as fluorescent labels, many fluorescent patterns can thus be generated, which is useful for discriminating many particles. By the quantum dots, it is possible to generate, for example, 100 to 1,000,000 kinds, 1,000 to 1,000,000 kinds, or 10,000 to 1,000,000 kinds of fluorescent patterns. In other words, in the present technology, a group of particles having many kinds of mutually different fluorescent patterns may be used.

The nucleic acid 92 bound to the particle main body 91 may have a predetermined base sequence.

As depicted inside the dotted-line region of FIG. 9, for example, the nucleic acid 92 may have, for example, a UMI (Universal Molecular Identifier) sequence 93 and a poly-T sequence 94 or the like.

In the case where plural nucleic acids 92 are bound to one particle main body 91, as depicted in FIG. 9, the plural nucleic acids have mutually different UMI sequences 94. As a result, the plural nucleic acids can be discriminated from one another.

The poly-T sequence 95 may be used, for example, for trapping mRNA by binding between the mRNA and a poly-A sequence.

The above-described nucleic acids 92 can be produced, for example, by a method known in this technical field. In addition, for binding the nucleic acids 92 to the particle, a technique known in this technical field may be used.

By performing the particle confirming method according to the present technology by use of the particles 90 described above, it is possible, for example, to efficiently perform sample preparation for single cell sequencing and a single cell sequencing treatment. An example of a nucleic acid sequencing treatment using the particles 90 and including the particle confirming method according to the present technology will be described referring to FIGS. 1 and 11. FIG. 1 is the same as described above. FIG. 11 illustrates schematic diagrams for explaining a particle confirming treatment of the present technology.

In step S101, the nucleic acid sequencing treatment including the particle confirming method of the present technology is started. Prior to the start of the nucleic acid sequencing treatment, a fluid containing the aforementioned particles 90 and a particle trapping chip including a particle trapping region having at least one well are prepared. The particle trapping chip may be, for example, as depicted in FIGS. 2A and B described in "(2) First example of first embodiment (Particle fractionating method)" above.

(3-1A) Trapping Step

In step S102, the particles 90 are trapped in wells 205 provided in a particle trapping region 204, whereby a state as depicted in FIG. 11(a) is formed. For forming the state, for example, an operation as described in "(2-1) Trapping step" above may be performed. In FIG. 11(a), the particles trapped in the wells have mutually different kinds of fluorescence as ID information. That the particles have mutually different kinds of fluorescence is represented by the differences between the patterns imparted to the particles 90 in FIG. 11(a).

(3-2A) Correlating Step

In step S103, the fluorescence possessed by the particle main body 91 of the particle 90 is acquired as ID information. Further, in step S103, the pieces of ID information and the pieces of position information of the wells 205 in which the particles 90 are trapped respectively are correlated. The position information may be the information as described in "(2-2) Correlating step" above.

In step S103, further, cells as objects of sequence are trapped in the wells. For the trapping, for example, the operation as described in "(2-1) Trapping step" above may be conducted. As a result, as depicted in FIG. 11(b), a state in which one particle 90 and one cell 250 are trapped in each well is formed. For example, as depicted in FIG. 12(a), each well 205 may be formed with two holes 206-a and 206-b, and the particle 90 and the cell 250 may be maintained at entrances of the two holes by suction through the holes, for example. Alternatively, as depicted in FIG. 12(c), each well may be formed with one slit-like well 206-c, and the particle 90 and the cell 250 may be maintained in the one slit-like well by suction.

In step S103, in addition to the fluorescence or in place of the fluorescence, an image of the particle 90 and/or an image of the cell 250 may be acquired as ID information. These images may be acquired, for example, by an imaging device (a camera or the like) through a microscope. The image may include a characteristic (for example, a characteristic in shape) of the particle 90 or the cell 250. In step S103, these images may be correlated with the above-mentioned position information.

After the correlation is completed, the cell 250 is dissolved, and a cell-derived nucleic acid (for example, mRNA or the like) 251 possessed by the cell 250 is bound to the nucleic acid 92 possessed by the particle 90. A technique for dissolving the cell 250 may be selected, as required, by a person skilled in the art. The binding may be, for example, binding between a poly-T sequence of the nucleic acid 92 and a poly-A sequence of the cell-derived nucleic acid 251. As a result of the binding, as depicted in FIG. 12(b), for example, a state in which the cell-derived nucleic acid 251 is bound to the particle 90 through the nucleic acid 92 is formed.

(3-3A) Discharging Step

In step S104, the particles 90 may be discharged from the wells 205 one by one, or the particles 90 may be simultaneously discharged from all the wells 205 in the particle trapping region 204. A discharging treatment in which the particles 90 are discharged one by one may be conducted, for example, as described in "(2-3) Discharging step" above. For a discharging treatment in which the particles 90 are simultaneously discharged, for example, the whole surface of the particle trapping region 204 may be irradiated with laser light, or such a flow that the particles are discharged from all the wells may be formed in the vicinity of the particle trapping region 204.

(3-4A) Particle Moving Step

In step S105, the particles 90 discharged from the wells are moved from the particle trapping region 204, and are recovered into a container outside of the particle trapping region 204. The movement may be performed, for example, as described in "(2-4) Particle moving step" above.

(3-5A) ID Information Acquiring Step

In step S106, the sequence of the cell-derived nucleic acids 251 bound to the particles 90 through the nucleic acids 92 is sequenced, and the sequence of the cell-derived nucleic acids 251 is acquired as ID information. Further, in step S106, in addition to the sequence of the cell-derived nucleic acids 251, for example, fluorescence and/or mages of the particles 90 may be acquired as ID information. A combination of the sequence of the cell-derived nucleic acids 251 and the fluorescence and/or images of the particles 90 may be ID information acquired in step S106.

The sequence may be performed, for example, by what is generally called a next-generation sequencing treatment. As a kind of the next-generation sequencing treatment and a device for the sequencing treatment to be used, a treatment and device known in this technical field may be used. For example, the cell-derived nucleic acid 251 bound to the particle 90 may be fragmented, as required, and an adaptor may be subjected to ligation. After the ligation, the fragment of the cell-derived nucleic acid 251 to which the adaptor is added is fixed on a substrate, and bridge PCR is conducted on the substrate. By the bridge PCR, a cluster is formed. After the cluster formation, Sequencing-by-Synthesis, for example, may be performed. As a result, sequence data of the cell-derived nucleic acids 251 can be obtained.

(3-6A) Confirming Step

As aforementioned, the ID information acquired in step S106 may include the fluorescence and/or images of the particles 90, in addition to the sequence of the cell-derived nucleic acids 251. The sequence and the fluorescence and/or images may be correlated in step S107. Note that the correlation may be carried out in step S106.

As above-mentioned, the fluorescence and/or images of the particles 90 are acquired as ID information in step S103, and the ID information is correlated with pieces of the position information of the wells in which the particles 90 have been trapped. The fluorescence and/or image of the particle 90 acquired in step S103 corresponds to the fluorescence and/or image of the particle 90 acquired in step S106, and this is correlated with the sequence of the cell-derived nucleic acids 251. Therefore, through the fluorescence and/or image of the particle 90, it is possible to confirm whether the cell having the sequence of the cell-derived nucleic acids 251 acquired in step S106 has been trapped in the well having the above-mentioned position information. As a result, for example, the sequence of the cell-derived nucleic acids 251 and the image of the cell 250 (particularly, a characteristic of the cell) can be correlated with each other.

(4) Example of Particle

In the present technology, the particles are, for example, those which are required to be trapped one by one. Examples of the particles include cells, micro-organisms, biological solid components, biological fine particles such as liposomes, and synthetic particles such as latex beads, gel beads, magnetic beads, and quantum dots, but these are not limitative. The cells may include animal cells and plant cells. Examples of the animal cells include tumor cells and blood cells. The micro-organisms may include bacteria such as *E. coli*, and fungi such as yeast. Examples of the biological solid components include solid crystals generated in the living bodies. The synthetic particles may be, for example, particles of organic or inorganic polymer materials, metals, etc. The organic polymer materials may include polystyrene, styrene-divinylbenzene, and polymethacrylate. The inorganic polymer materials may include glass, silica and magnetic materials. The metals may include gold colloid and aluminum. In addition, in the present technology, the particles may be bound substances of plural particles, such as two or three particles.

According to one embodiment of the present technology, the particles may be, for example, cells, micro-organisms, biological solid components, biological fine particles such as liposomes, particularly cells. For example, the particle fractionating method of the present technology may be used for fractionation of cells.

According to another embodiment of the present technology, the particles may be synthetic particles such as latex beads, gel beads, and magnetic beads, particularly synthetic particles having a fluorescent label. The particle confirming method of the present technology may be conducted, for example, in a nucleic acid sequencing treatment using the synthetic particles.

In the present technology, the particles may be served to the particle fractionating method of the present technology, preferably in the state of being contained in a fluid. The fluid includes liquids and gases. Preferably, the fluid is a liquid. The kind of the liquid may be selected, as required, according to the kind of the particles by a person skilled in the art. In the case where the particles are cells, for example, as the liquid may be used, for example, water, aqueous solutions (for example, buffer solutions), or culture media.

2. Second Embodiment (Particle Trapping Chip)

(1) Description of Second Embodiment

The present technology provides a particle trapping chip that includes a particle trapping region having at least one well, in which each of the at least one well has a label element capable of being transferred from the well to a particle. Each well in the particle trapping region has a label element that can be transferred to the particle. Therefore, ID information can be added to the particle trapped in the well, and, further, the particle with the ID information added thereto can be discharged from the well. Therefore, the particle trapping chip is suitable for carrying out the particle fractionating method according to the present technology that has been described in "1. First embodiment (Particle fractionating method)" above. In other words, the particle trapping chip may be one to be used in the particle fractionating method according to the present technology.

(2) Example of Fixation of Label Element to Well

According to one embodiment of the present technology, the label element may be fixed to each well through a linker. The fixation of the label element through the linker can preferably be canceled. In order that the fixation can be canceled, for example, the linker may be able to liberate the label element, or the linker itself can be decomposed or can be cut.

The linker capable of liberating the label element may be a linker such that the bond between the linker and the label element can be cut. The decomposable or cuttable linker may be a linker capable of canceling the fixation of the label element, by a fact that the chemical structure of the linker itself is decomposable or that at least one part inside the chemical structure of the linker itself is cuttable.

In order to cancel the fixation, a physical treatment with, for example, light, heat or the like or a chemical treatment with, for example, an enzyme or pH may be performed. Preferably, the treatment for canceling the fixation is a light irradiation treatment, more preferably a treatment of irradiation with light other than visible light, and further preferably a treatment of irradiation with ultraviolet light (UV light) or infrared light (IR light). The light irradiation treatment may be applied, for example, to only the well in which the particle to be fractionated is trapped, or to a partial region or the whole region of the particle trapping region.

The linker is preferably a photodegradable linker. The photodegradable linker is a molecule having such a structure as to be decomposed by irradiation with light having a specific wavelength. The wavelength used for the decomposition may be substantially coincident with the absorption wavelength of the molecule.

The photodegradable linker may have, for example, a methoxynitrobenzyl group, a nitrobenzyl group, a parahydroxyphenacyl group, a 7-nitroindoline group, a 2-(2-nitrophenyl)ethyl group, or a (cumarin-4-yl)methyl group as a structure decomposed by the irradiation with light. For example, a molecule having the methoxynitrobenzyl group may be decomposed by light having a wavelength of approximately 365 nm, for example. As a molecule having such a decomposable structure, molecules known in this technical field may be used in the present technology. In the present technology, for example, a 3-amino-3-(2-nitrophenyl)propionic acid (ANP) group, a 4-[4-(1-{[(1H-fluoren-9-ylmethoxy)carbonyl]amino}ethyl)-2-methoxy-5-nitrophenoxy]butanoic acid group, or a 4,5-dimethoxy-2-nitrobenzyl group may be used as the photodegradable linker.

For instance, examples of the enzyme degradable linker include glucuronic acid, Val-Leu-Lys tripeptide, oligonucleic acid, cellulose, polylactic acid, and ENLYFQ(G/S) peptide. Examples of the linker dissociated in response to pH include polyhistidine peptide. In the present technology, these linkers may be used for fixing the label element to the well.

(3) Example of Coupling Mode Between Label Element and Particle

The coupling mode between the label element and the particle may be selected, as required, by a person skilled in the art, and techniques known in this technical field may be adopted. For example, by coupling between the particle (particularly, a substance present on the particle surface) and a label element holding substance coupled to the linker, the label element and the particle may be coupled to each other through the holding substance. Alternatively, by coupling between the particle (particularly, a substance present on the particle surface) and a particle coupling substance possessed by a label element holding substance coupled to the linker, the label element and the particle may be coupled to each other through the holding substance. The coupling mode between the label element and the particle will be described below referring to FIGS. 13 and 14.

FIG. 13 illustrates schematic diagrams depicting that by coupling between a compound present on the particle surface and a label element holding substance coupled to the linker, the label element and the particle are coupled to each other through the holding substance.

FIG. 13(a) is a schematic diagram depicting a situation in which a fluorescent substance as a label element is fixed to the well surface.

As depicted in FIG. 13(a), a photodegradable linker 302 is coupled to a surface 301 of a well 300. The oligonucleic acid 303 as a label element holding substance is coupled to the photodegradable linker 302, and a fluorescent substance 304 is coupled to the oligonucleic acid 303. In other words, the oligonucleic acid 303 having the fluorescent substance 304 is fixed to the well 300 through the photodegradable linker 302.

An example of trapping of the particle into the well 300 and transfer of the label element to the particle is depicted in FIGS. 13(b) to (d).

FIG. 13(b) is a schematic diagram depicting a state before the particle is trapped in the well 300. As illustrated in FIG. 13(b), the particle trapped in the well 300 is a cell 305. A DNA 307 complementary to the oligonucleic acid 303 is coupled to the cell 305 through an antibody 306 that is coupled to a surface antigen of the cell 305.

FIG. 13(c) is a schematic diagram depicting a state in which the particle is trapped in the well 300. As illustrated in FIG. 13(c), with the cell 305 entering the well 300, the DNA 307 present on the surface of the cell 305 is brought into hybridization with the oligonucleic acid 303 fixed to the well 300. By the hybridization, the cell 305 is labeled with the fluorescent substance 304 as a label element. In such a way, ID information is imparted to the cell 305.

Next, the well 300 is irradiated with UV light. By the irradiation, the photodegradable linker 302 is decomposed. By the decomposition, the oligonucleic acid 303 having the fluorescent substance 84 is liberated from the surface 301 of the well 300. The oligonucleic acid 303 having the fluorescent substance 304 is coupled to the DNA 307 on the surface of the cell 305 by the hybridization. Therefore, as depicted in FIG. 13(d), the cell 305 may be discharged from the well 300 in the state of being labeled with the fluorescent substance 304.

In addition, a combination of biotin and avidin may be used in place of the combination of the oligonucleic acid 303 and the DNA 307.

Figure 14:
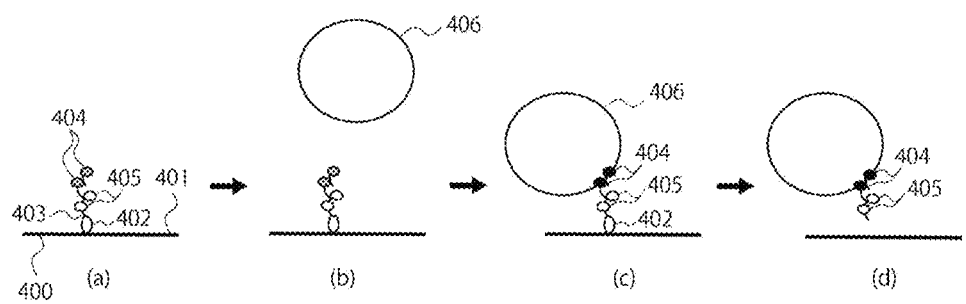
FIG. 14 illustrates other diagrams for explaining a coupling mode between a label element and a particle.

FIG. 14 illustrates schematic diagrams depicting that, by coupling between a compound present on the particle surface and a particle coupling substance possessed by a label element holding substance coupled to a linker, the label element and the particle are coupled to each other through the holding substance.

FIG. 14(a) is a schematic diagram depicting a situation in which a fluorescent substance as a label element is fixed to the well surface.

As illustrated in FIG. 14(a), a photodegradable linker 402 is coupled to a surface 401 of a well 400. A label element holding substance 403 (for example, oligonucleic acid, PEG, etc.) is coupled to the photodegradable linker 402, and FITC 404 as a fluorescent substance and a second fluorescent substance 405 (a substance that extinguishes more slowly than FITC, for example, rhodamine or the like) other than FITC 404 are coupled to the label element holding substance 403. In other words, FITC 404 and the second fluorescent substance 405 are fixed to the well 400 through the photodegradable linker 402.

FITC 404 is one of fluorescent dyes that extinguishes fast. A fluorescent dye is turned into a radical at the time of extinction, and the dye turned into the radical may be coupled to a substance present in the vicinity. In view of this, the FITC 404 is used as a particle coupling substance.

An example of trapping of a particle into a well 400 and transfer of a label element to the particle is depicted in FIGS. 14(b) to (d).

FIG. 14(b) is a schematic diagram depicting a state before the particle is trapped in the well 400. As illustrated in FIG. 14(b), the particle trapped in the well 400 is a cell 406.

FIG. 14(c) is a schematic diagram depicting a state in which the particle is trapped in the well 400. When the well 400 is irradiated with exciting light of 488 nm, for example, after the cell 406 is trapped in the well 400, FITC 404 is excited. Thereafter, FITC 404 is turned into a radical attendant on extinction. FITC 404 turned into a radical is coupled to the cell 406, as depicted in FIG. 14(c). On the other hand, the second fluorescent substance 405 does not extinguish.

Therefore, the cell 406 is labeled with the second fluorescent substance 405 as a label element. In this way, ID information is imparted to the cell 406.

Next, the well 400 is irradiated with UV light. By the irradiation, the photodegradable linker 402 is decomposed. By the decomposition, the label element holding substance 403 having the second fluorescent substance 405 is liberated from the surface 401 of the well 400. The label element holding substance 403 having the second fluorescent substance 405 is coupled to the cell 405 through the coupling between FITC 404 and the cell 405. Therefore, the cell 405 may be discharged from the well 400 in the state of being labeled with the second fluorescent substance 405, as depicted in FIG. 14(d).

In the present embodiment, nucleic acid may be fixed to a well without using fluorescence. An example of the particle confirming method according to the present technology in this case will be described in (3-1B) to (3-6B) below, referring to FIGS. 1 and 17.

(3-1B) Trapping Step

In step S102, a cell 262 is trapped in a well 261 provided in a particle trapping region, whereby a state as depicted in FIG. 17(a) is formed. FIG. 18 depicts an enlarged view of the trapped cell.

The cell 262 has antibodies 263 coupled to surface antigens of the cell 262. A nucleic acid 264 is coupled to the antibody 263. On the other hand, oligonucleic acid 267 having a bar code array region 266 is fixed to the well 261 through a photodegradable linker 265, for example. The cell 262 enters the well 261 from the outside. Then, oligonucleic acid 267 fixed to the well 261 and the nucleic acid 264 possessed by the cell 262 are put into hybridization, whereby the cell 262 is trapped in the well 261. The region having undergone the hybridization is denoted by reference sign 268.

The bar code array may be an array generated based on a bar coding technology, and may, more specifically, be a DNA bar code array or an RNA bar code array. For example, different bar code arrays may be allotted to the wells.

(3-2B) Correlating Step

In step S103, fluorescence possessed by the cell 262 and/or an image of the cell 262 is acquired as ID information. Further, in step S103, the ID information and position information of the well 261 in which the cell 262 is trapped are correlated with each other. The position information may be information as described in "(2-2) Correlating step" above.

(3-3B) Discharging Step

In step S104, the cell 262 is discharged from the well 261. A treatment for the discharge may be conducted, for example, as described in "(2-3) Discharging step" above. For example, the discharge is performed by decomposing the photodegradable linker 265 by irradiation with predetermined light.

(3-4B) Particle Moving Step

In step S105, the cell 262 discharged from the well is moved from the particle trapping region and is recovered into a container outside the particle trapping region, as depicted in FIG. 17(b). The movement may be conducted, for example, as described in "(2-4) Particle moving step" above.

(3-5B) ID Information Acquiring Step

In step S106, fluorescence possessed by the cell 262 and/or an image of the cell 262 is acquired. The acquisition may be performed, for example, during the particle moving step, or may be conducted after the particle moving step.

In step S106, further, the oligonucleic acid 267 having the bar code array region 266 is dissociated from the nucleic acid 264, as depicted in FIG. 17(c). The dissociation may be conducted, for example, by lowering the temperature of a nucleic acid hybrid containing liquid and keeping the liquid to stand for a while. After the dissociation, the sequence of the oligonucleic acid 267 having the bar code array region 266 is acquired by a sequence treatment. The sequence treatment may be performed, for example, by what is generally called a next-generation sequencing treatment. By the sequence treatment, the sequence of the region 268 having undergone the hybridization is acquired.

In step S106, the fluorescence and/or the image may be correlated with the sequence.

A combination of the fluorescence possessed by the cell 262 and/or the image of the cell 262 with the sequence is used as ID information in the following confirming step.

(3-6B) Confirming Step

As has been aforementioned, the ID information acquired in step S103 is correlated with the position information of the well in which the cell 262 has been trapped. The ID information (the fluorescence and/or the image of the cell 262) acquired in step S103 corresponds to the ID information (the fluorescence and/or the image of the cell 262) acquired in step S106. The latter ID information is correlated with the sequence (inclusive of the sequence of the region 268 having undergone hybridization) of the oligonucleic acid 267. Therefore, whether the cell having been coupled to the sequence acquired in step S106 has been trapped in the well having the position information can be confirmed, through the ID information (the fluorescence and/or the image of the cell 262). As a result, for example, the sequence of the region 268 having undergone the hybridization and the image (particularly, a characteristic of the cell) of the cell 262 can be correlated with each other.

(4) Example of Layout of Label Elements

According to one embodiment of the present technology, the adjacent wells in the particle trapping region may have different label elements. With the adjacent wells having the different label elements, it is easy, for example, to confirm whether the particle having acquired ID information in the ID information acquiring step of the particle fractionating method of the present technology is the particle having been trapped in the well having the position information correlated in the correlating step. The description in "(2-1) Trapping step" of "1." above applies also to the present embodiment.

According to another embodiment of the present technology, the wells in the particle trapping region may be disposed such as to form a plurality of columns, and the adjacent two columns may have mutually different label elements.

According to a further embodiment of the present technology, the particle trapping region may be divided into a plurality of regions. Further, the wells constituting the plurality of regions may have different label elements.

The description in "(2-1) Trapping step" of "1." above is applied also to these embodiments.

(5) First Example of Particle Trapping Chip

Examples of the particle trapping chip of the present technology include the particle trapping chip 101 included in the particle trapping chamber described referring to FIGS. 2A and B in (2) of "1." above. As aforementioned, the particle trapping chip 101 is such that the particle is lowered in the particle trapping space 109 and is trapped in the well 105.

(6) Second Example of Particle Trapping Chip

Figure 15:
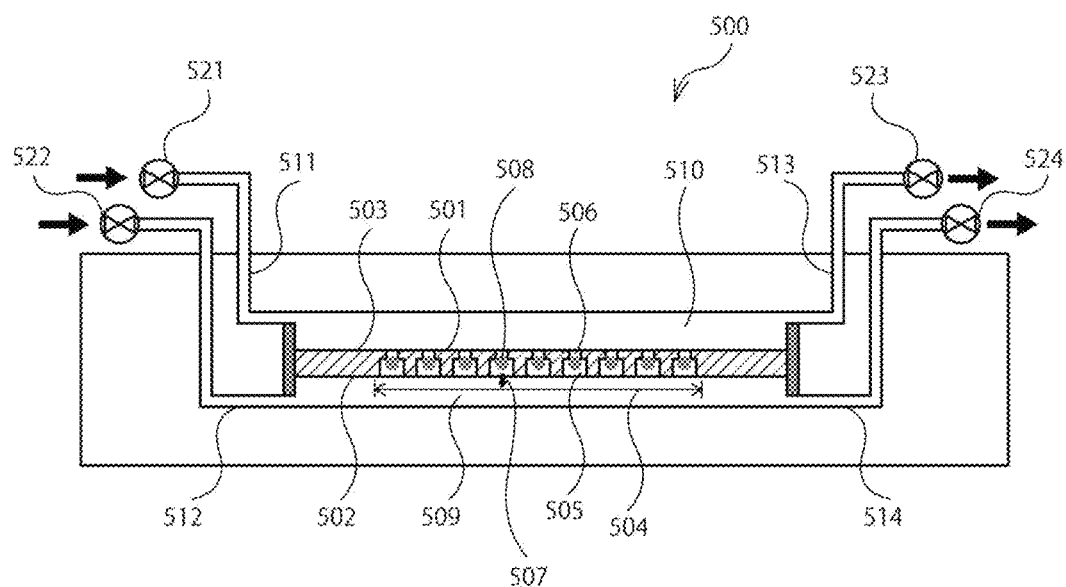
FIG. 15 is a schematic diagram depicting an example of a particle trapping chamber used in the particle confirming method according to the present technology.

Another example of the particle trapping chip of the present technology will be described below, referring to FIG. 15. FIG. 15 is a schematic diagram of a particle trapping chamber including the particle trapping chip according to the present technology.

A particle trapping chamber 500 described in FIG. 15 includes a particle trapping chip 501. Wells 505 of the particle trapping chip 501 are opened toward the sedimentation side of the particles, conversely to the wells 105 of the particle trapping chamber 100 in FIG. 2A.

The particle trapping chip 501 has a particle trapping surface 502 and a surface 503 directed to the opposite side. The particle trapping surface 502 is provided with a particle trapping region 504, and the particle trapping region 504 includes a plurality of wells 505. The well 505 has such a size that the particle can be accommodated in the inside of the well 505. Holes 506 are provided in respective bottom portions of the wells 505. The hole 506 penetrates from the bottom portion of the well to the surface 503 on the opposite side. The hole 506 has such a size that the particle does not pass therethrough.

Note that FIG. 15 is a schematic diagram depicting a state in which particles 508 are trapped in the wells 505, and the particles 508 may not be present in the well 505 before the start of a particle trapping treatment.

To the material and producing method of the particle trapping chip 501 (particularly, the region where the wells 505 are formed), the above description concerning the particle trapping chip 101 in FIGS. 2A and B applies. To the shape and layout of the wells 505 and the material of other parts of the particle trapping chamber 500, also, the above description regarding the particle trapping chip 101 and the particle trapping chamber 100 in FIGS. 2A and B applies.

The inside of the particle trapping chamber 500 is partitioned into two spaces by the particle trapping chip 501. The space on the side on which the wells 505 are opened is referred to as a particle trapping space 509, and the space on the other side is referred to as an other-side space 510.

The particle trapping chamber 500 is disposed such that gravity acts on the particle 508 in the direction of an arrow 507.

As depicted in FIG. 15, the particle trapping chamber 500 includes a first fluid supply channel section 511, a second fluid supply channel section 512, a first fluid discharge channel section 513, and a second fluid discharge channel section 514. The first fluid supply channel section 511 and the first fluid discharge channel section 513 are connected to the other-side space 510. The second fluid supply channel section 512 and the second fluid discharge channel section 514 are connected to the particle trapping space 509.

The first fluid supply channel section 511, the second fluid supply channel section 512, the first fluid discharge channel section 513, and the second fluid discharge channel section 514 are provided with valves 521, 522, 523, and 524, respectively.

Pumps (not illustrated) are connected to these four channel sections, respectively. With the pumps driven, a fluid can be supplied into the particle trapping chamber 500 through these four channel sections, or the fluid can be sucked from the inside of the particle trapping chamber 500 through these four channel sections. These four pumps can be controlled independently from one another.

In the case of performing the particle fractionating treatment inclusive of the particle confirming method according to the present technology by use of the particle trapping chamber 500, the particle fractionating treatment may include the steps conducted in the particle fractionating treatment described in "(2) First example of first embodiment (Particle fractionating treatment including performing particle confirming method of the present technology)" above. The outline of each step will be described below. To details of each step, the contents described in "(2) First example of first embodiment (Particle fractionating treatment including performing particle confirming method of the present technology)" above apply.

In regard to "(2-1) Trapping step" above, a particle-containing liquid is supplied through the second fluid supply channel section 512 into the particle trapping space 509. Simultaneously with the supply, suction through the first fluid discharge channel section 513 (and, if required, through the first fluid supply channel section 511) may be conducted. As a result, the particle 508 is raised inside the particle trapping space 509, and is trapped in the well 505.

The particle trapped into the well 505 may be labeled with a label element fixed to the inside of the well 505 through a linker. The label element may be, for example, a fluorescent dye, a color, an electric charge, a magnetic charge, an oligonucleic acid, or a peptide.

In regard to "(2-2) Correlating step" above, pieces of ID information possessed by the particles 508 trapped respectively in the plurality of wells 505 in the particle trapping region 504 and pieces of position information of the wells in which the particles 508 are trapped are correlated. The correlation may be conducted, for example, with respect to only the wells in which the particles having fluorescence indicative of the desired particles are trapped, or may be performed with respect to the wells in a partial region of the particle trapping region 504, or may be conducted with respect the whole region of the particle trapping region 504. For performing the correlation, the image acquiring step described in "(2-2) Correlating step" above may be conducted.

In regard to "(2-3) Discharging step" above, the desired particles are discharged from the wells 505 in which the desired particles are trapped. Prior to the discharge, the fixation of the label element to the well may be canceled. For example, by cutting the linker by irradiation with UV rays, the fixation can be canceled. After the fixation is canceled, for example, suction through the second fluid discharge channel section 514 and liquid supply through the first fluid supply channel section 511 may be conducted. As a result, the particles 508 are discharged from the wells 505.

In regard to "(2-4) Particle moving step" above, the suction through the second fluid discharge channel section 514 and the liquid supply through the first fluid supply channel section 511 which are conducted for discharging the particles 508 from the wells 505 are continued, whereby the particles 508 go from the particle trapping space 509 into the second fluid discharge channel section 514. For example, a tube (not illustrated) is connected to the second fluid discharge channel section 514. The particles 508 may pass through the second fluid discharge channel section 514 and the tube, to be recovered into a container or onto a well plate (not illustrated) for particle recovery.

In regard to "(2-5) ID information acquiring step" above, ID information of the particles 508 recovered into the container or onto the well plate is acquired. As the ID information, for example, fluorescence possessed by the particle may be acquired.

In regard to "(2-6) Confirming step" above, it is confirmed whether the ID information acquired in the ID information acquiring step is the same as the ID information used for correlation in the correlating step. By a condition that both pieces of ID information are the same, it is confirmed that the particles recovered are the desired particles. By a condition that both pieces of ID information are not the same, it is confirmed that the particles recovered are not the desired particles.

3. Third Embodiment (Particle Analyzing System)

(1) Description of Third Embodiment

A particle analyzing system according to the present technology includes the followings, at least: a particle trapping chip which includes a particle trapping region having at least one well, and in which each of the at least one well has a label element capable of being transferred from the well to a particle; a particle recovering section that recovers the particle discharged from the at least one well; and an ID information acquiring section that acquires ID information possessed by the discharged particle. With each of the at least one well having the label element capable of being transferred from the well to the particle, it is possible to perform the correlating step in the particle confirming method according to the present technology, and, in addition, to impart ID information to the particle discharged from the well. Further, since the ID information acquiring section acquires the ID information possessed by the particle discharged from the well, the confirming step in the particle confirming method according to the present technology can be performed, on the basis of the ID information possessed by the particle discharged from the well. Therefore, it is possible to confirm whether the desired particle has been fractionated, by the particle analyzing system. In such a way, the method according to the present technology can be performed, for example, by the particle analyzing system according to the present technology.

(2) Example of Third Embodiment (Particle Analyzing System)

Figure 16:
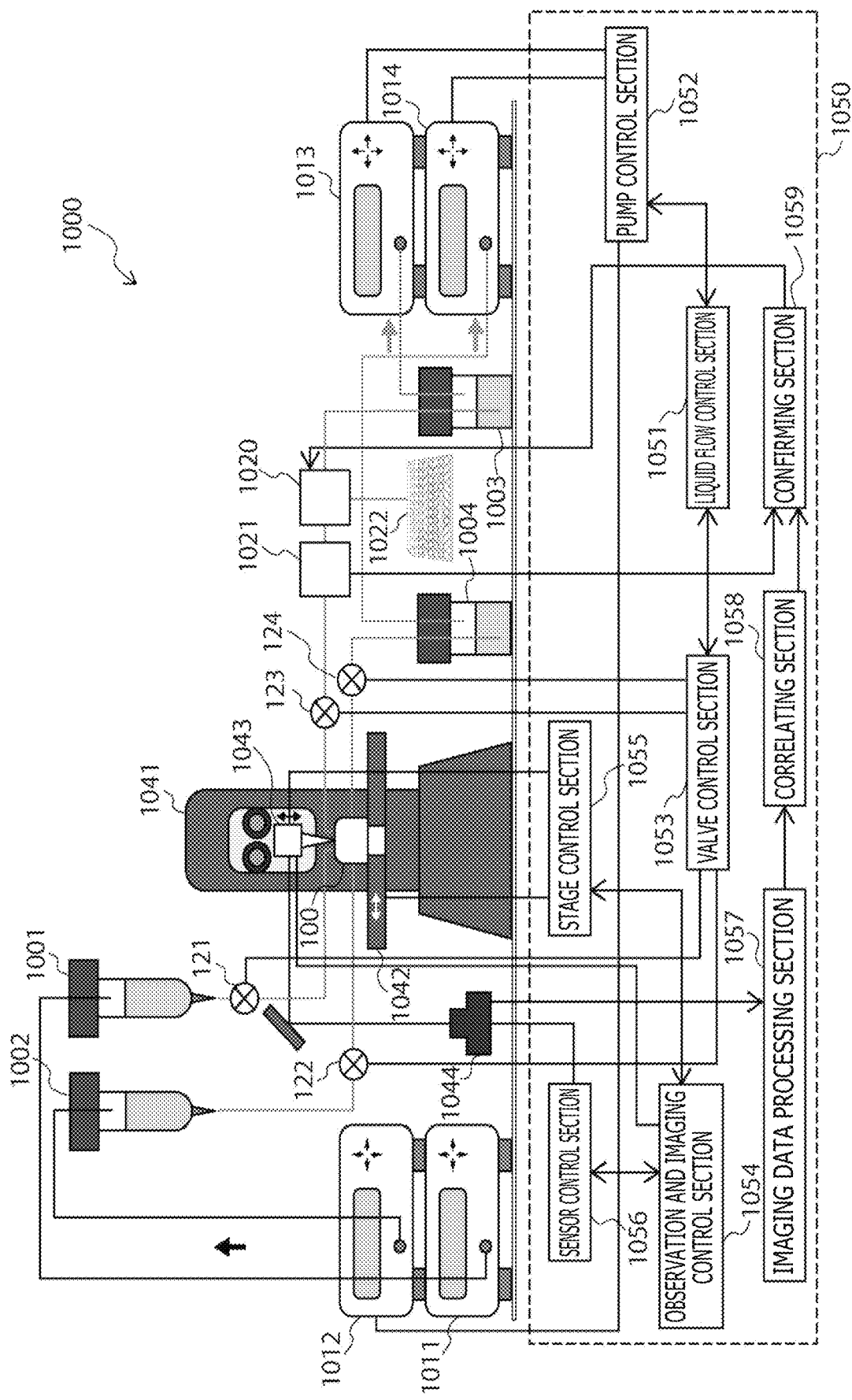
FIG. 16 is a diagram depicting a configuration example of a particle analyzing system according to the present technology.

An example of a particle analyzing system according to the present technology will be described referring to FIG. 16. FIG. 16 is a configuration example of the particle analyzing system of the present technology.

A particle analyzing system 1000 of the present technology illustrated in FIG. 16 includes a particle trapping chamber 100. The particle trapping chamber 100 is as described in "(2) First example of first embodiment" of "1." above, and the description applies also to the present embodiment.

A liquid supply tank 1001 is connected through a valve 121 to a first fluid supply channel section 111, of constituent elements of the particle trapping chamber 100. A minute pressure pump 1011 is connected to the liquid supply tank 1001.

In addition, a liquid supply tank 1002 is connected to a second fluid supply channel section 112 through a valve 122. A minute pressure pump 1012 is connected to the liquid supply tank 1002.

A fractionation control section 1020 is connected to a first fluid discharge channel section 113 through a valve 123. The fractionation control section 1020 causes a particle confirmed to be a desired particle to go to a particle recovering section 1022. The fractionation control section 1020 causes a particle not confirmed to be a desired particle to go to a waste liquid tank 1003. For causing the particle to go from the particle trapping chamber 100 toward the fractionation control section 1020, for example, a minute pressure pump 1013 is connected to the waste liquid tank 1003. In addition, the fractionation control section 1020 may include a minute pressure pump (not illustrated), and, by the minute pressure pump, the going of the particle to the particle recovering section 1022 or the waste liquid tank 1003 can be controlled.

In addition, a second fluid discharge channel section 114 is provided with a waste liquid tank 1004 and a minute pressure pump 1014 through a valve 124.

These valves may be preferably electrically driven type pinch valves. Besides, these minute pressure pumps are preferably able to adjust pressure in a range of 10 to 3,000 Pa, more preferably 100 to 2,000 Pa, for example, 100 to 1,000 Pa at intervals of preferably 10 to 300 Pa, more preferably at intervals of 20 to 200 Pa.

The particle trapping chamber 100 is disposed on a stage 1042 of a microscope 1041. The stage 1042 can be moved by electrical control, and can be moved, for example, in X and Y directions.

An objective lens 1043 of the microscope 1041 can be moved by electrical control, and can be moved, for example, in a Z direction. The objective lens 1043 is configured such that a particle trapping surface of the particle trapping chamber 100 can be observed from above the particle trapping chamber 100.

The microscope 1041 may be provided with, for example, a light source (e.g., laser, halogen lamp, mercury lamp, or LED), a filter (e.g., excitation filter and/or fluorescent filter), objective lenses of magnifications according to the purpose, an electrically driven XY stage, and an electrically driven Z stage (which may be one for moving the objective lens or a stage for placing the chamber). A camera 1044 is connected to the microscope 1041. The camera 1044 is configured such that the particle trapping surface of the particle trapping chamber 100 can be imaged through the objective lens 1043. The camera 1044 includes, for example, a CMOS or CCD image sensor. The camera 1044 is configured such as to be able to transmit imaging data to an imaging data processing section which will be described below.

The particle analyzing system 1000 is provided with a control section 1050. The control section 1050 includes a liquid flow control section 1051, a pump control section 1052, a valve control section 1053, an observation and imaging control section 1054, a stage control section 1055, a sensor control section 1056, and an imaging data processing section 1057. The control section 1050 may include, for example, a hard disk in which a program and an OS for causing the minute confirming method according to the present technology to be executed by the particle analyzing system 1000 are stored, a CPU, and a memory. For example, the function of the control section 1050 may be realized by a multipurpose computer. The program may be recorded on a recording medium such as, for example, micro SD memory, an SD memory card, or a flash memory. The program recorded on the recording medium may be read out by a drive provided in the particle fractionating system 1000, then the control section 1050 may control each element constituting the particle analyzing system 1000, for example, according to the program read out, whereby the particle confirming method according to the present technology may be carried out.

The liquid flow control section 1051 controls the pump control section 1052 and the valve control section 1053, to control the supply of a fluid to the particle trapping chamber 100 or the discharge of the fluid from the particle trapping chamber 100. The liquid flow control section 1051 controls, for example, capture of cells, exchanges of chemicals, and/or recovery of the cells. The liquid flow control section 1051 may control flows of a fluid for performing the trapping step described in "(2-1) Trapping step" of "1." above, the discharging step described in "(2-3) Discharging step" of "1." above, and the particle moving step described in "(2-4) Particle moving step" of "1." above.

The pump control section 1052 controls operations of the minute pressure pumps and/or differential pressures imparted by the minute pressure pumps.

The valve control section 1053 controls the opening and closing of the valves.

The observation and imaging control section 1054 controls the stage control section 1055 and the sensor control section 1056, to image the particle trapping surface. The observation and imaging control section 1054 controls the stage control section 1055 and the sensor control section 1056.

The stage control section 1055 controls the stage 1042 and/or the objective lens 1043. By the stage control section 1055, the region to be imaged may be moved and/or the focus may be adjusted.

The sensor control section 1056 controls the camera 1044. By the sensor control section 1056, for example, the timing of imaging of the particle trapping surface, exposure period, and/or the number of times of imaging may be controlled.

By the observation and imaging control section 1054, control of the stage by the stage control section 1055 and control of camera operation by the sensor control section 1056 may be synchronized. The observation and imaging control section 1054 may control the rotation of an electrically driven revolver to which plural objective lenses 1043 are attached. In other words, the observation and imaging control section 1054 can switch the objective lenses 1043.

The imaging data processing section 1057 processes imaging data transmitted from the camera 1044. For example, in the case where the particle trapping surface is imaged by dividing it into a plurality of regions, the imaging data processing section 1057 may generate single imaging data concerning the whole part of the particle trapping surface from the imaging data of the plurality of regions. In addition, the imaging data processing section 1057 may correct the imaging data, as required, to generate imaging data from which desired ID information can easily be extracted.

Figure 17:
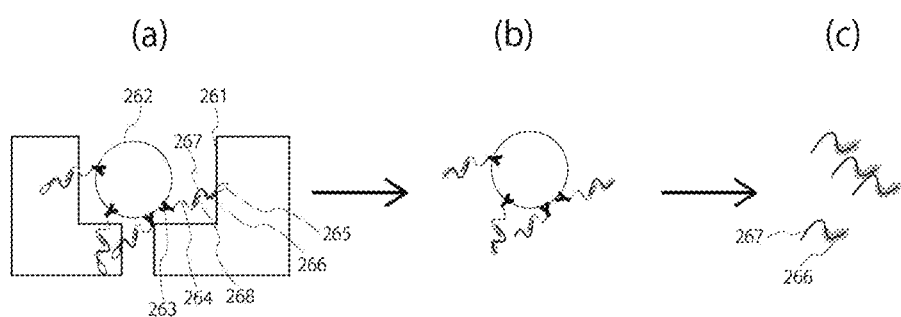
FIG. 17 illustrates diagrams depicting an example of the trapping and discharge of a particle in the method according to the present technology.
Figure 18:
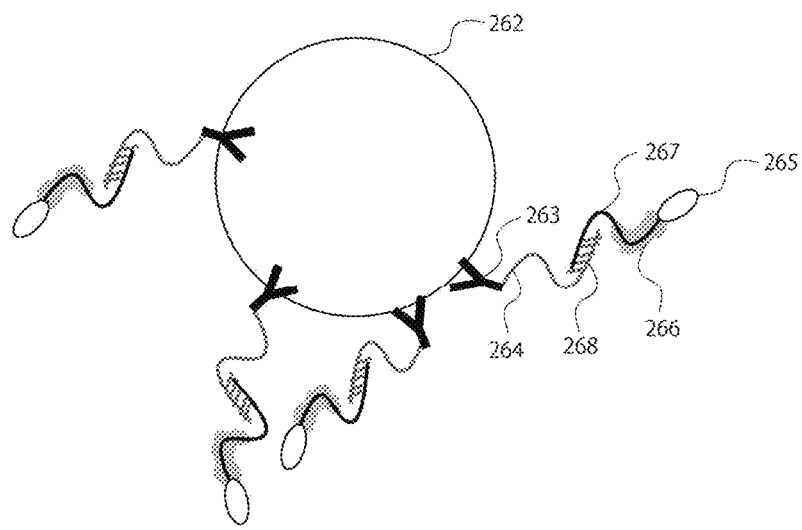
FIG. 18 is a schematic diagram of an example of a particle trapped in a well.

The control section 1050 further includes a correlating section 1058, as depicted in FIG. 17. The correlating section 1058 performs, for example, the correlating step described in "(2-2) Correlating step" of "1." above. For example, the correlating section 1058 acquires ID information of the particle trapped in the well and position information of the particle, on the basis of the imaging data acquired by the imaging data processing section 1057, and correlates the ID information and the position information thus acquired with each other. The ID information and the position information may be those as described in "(2-2) Correlating step" of "1." above. In addition, the ID information and the position information thus correlated with each other may be stored, for example, in a storing section (not illustrated) included in the particle analyzing system 1000.

The particle analyzing system 1000 include an ID information acquiring section 1021. The ID information acquiring section 1021 may perform the ID information acquiring step described in "(2-5) ID information acquiring step" of "1." above. The ID information acquiring section 1021 may detect, for example, fluorescence and/or scattered light obtained by irradiation of the particle flowing in a channel with laser light, and may acquire data concerning the fluorescence and/or scattered light detected as ID information. A specific configuration of the ID information acquiring section 1021 may be changed, as required, according to the kind of the ID information to be acquired.

The control section 1050 further includes a confirming section 1059. The confirming section 1059 confirms the position of the well in which the particle is trapped, on the basis of the ID information acquired by the ID information acquiring section 1021. More specifically, the confirming section 1059 may perform the confirming step described in "(2-6) Confirming step" of "1." above.

The confirming section 1059 may control the fractionation control section 1020 according to the result of the particle confirmation. For instance, in the case where the particle is confirmed to be the desired particle as a result of particle confirmation by the confirming section 1059, the confirming section 59 controls the fractionation control section 1020 to cause the particle to go to the particle recovering section 1022. In the case where the particle is not the desired particle as a result of the particle confirmation by the confirming section 1059, the confirming section 1059 controls the fractionation control section 1020 to cause the particle to go to the waste liquid tank 1003.

The particle recovering section 1022 is, for example, a 5 mL tube, or a well plate such as a 96-well plate or a 384-well plate. The desired particles are recovered into the particle recovering section 1022, while other particles than the desired particles are recovered into the waste liquid tank 1003. In addition, both the desired particles and the other particles than the desired particles may be recovered respectively into different two or more wells on one well plate.

Alternatively, a particle recovering container for recovering the particles in one space may be used in place of the particle recovering section 1022.

In regard to the present technology as described above, it is to be understood by those skilled in the art that various modifications, combinations, sub-combinations, or replacements may be possible within the scope of the present technology and equivalents thereof, according to, for example, design requirements or other factors.

Note that the present technology may take the following configurations.

[1]
A particle confirming method including:
  a correlating step of correlating identification information possessed by a particle trapped in a well in a particle trapping region with position information of the well;
  a discharging step of discharging the particle from the well;
  an identification information acquiring step of acquiring identification information of the particle after the discharging step; and
  a confirming step of confirming whether the particle has been trapped in the well possessing the position information, on the basis of the acquired identification information.

[2]
The particle confirming method according to [1], further including:
  a trapping step of trapping the particle through a linker fixed to the well in the particle trapping region.

[3]
The particle confirming method according to [2], in which
  the trapping step includes a labeling step of labeling the particle trapped in the well to impart identification information to the particle.

[4]
The particle confirming method according to [3], in which
  in the labeling step, the particle is labeled with fluorescence, a color, an electric charge, a magnetic charge, an oligonucleic acid, or a peptide to impart identification information to the particle.

[5]
The particle confirming method according to [3] or [4], in which
  in the labeling step, adjacent wells in the particle trapping region have different label elements, and the particles trapped in the adjacent wells are labeled with different label elements.

[6]
The particle confirming method according to [3] or [4], in which
  in the labeling step, the wells in the particle trapping region are arranged to form a plurality of rows or columns, the adjacent two rows or columns have mutually different label elements, and the particles trapped in the wells in the adjacent rows or columns are labeled with the different label elements.

[7]
The particle confirming method according to any one of [1] to [6], in which
  the correlating step further includes an image acquiring step of acquiring an image of the particle trapping region, and
  fluorescence, a color, or a size or shape of a particle is acquired from the image as identification information and the identification information and the position information are correlated with each other.

[8]
The particle confirming method according to any one of [1] to [7], in which
  in the discharging step, a plurality of particles having identification information is discharged successively.

[9]
The particle confirming method according to [8], in which
  in the confirming step, an order of discharge of the plurality of particles is referred to.

[10]
The particle confirming method according to [8] or [9], in which
  in the discharging step, the discharge is temporarily stopped after a predetermined number of particles are discharged successively.

[11]
The particle confirming method according to [8] or [9], in which
  in the discharging step, a particle to be a mark is discharged after a predetermined number of particles are discharged successively.

[12]
The particle confirming method according to [8] or [9], in which
  in the discharging step, two or more particles discharged successively have different pieces of identification information.

[13]
The particle confirming method according to [3], in which
  the particle trapping region is divided into a plurality of fields, and
  the well includes a label element for specifying the field in which the well is disposed.

[14]
The particle confirming method according to any one of [2] to [13], in which
the discharging step further includes a light irradiation step of irradiating the linker fixed to the well with light to cut the linker.

[15]
The particle confirming method according to any one of [1] to [14], in which
the particle confirming method further includes a particle moving step of causing the particle discharged from the well in the discharging step to pass through a channel, and
in the identification information acquiring step, the identification information is acquired from the particle passing through the channel or the particle having passed through the channel.

[16]
The particle confirming method according to any one of [1] to [15], in which
in the confirming step, a group of a predetermined number of successive particles is disposed of when an order of pieces of identification information of the particles discharged in the discharging step and an order of pieces of identification information of the particles acquired in the identification information acquiring step are different from each other.

[17]
The particle confirming method according to any one of [1] to [16], further including:
a particle fractionating step.

[18]
The particle confirming method according to any one of [1] to [16], in which
the particle trapped in the well in the correlating step has two or more different pieces of identification information.

[19]
The particle confirming method according to any one of [1] to [16], further including:
a nucleic acid sequence step of acquiring identification information of the particle by a nucleic acid sequence treatment, in the identification information acquiring step.

[20]
A particle trapping chip including:
a particle trapping region having at least one well, in which
each of the at least one well has a label element that is able to be transferred from the well to a particle.

[21]
The particle trapping chip according to [20], in which
the label element is fixed to each well through a linker, and the fixation of the label element through the linker is able to be canceled.

[22]
The particle trapping chip according to [20] or [21], in which
adjacent wells in the particle trapping region have different label elements.

[23]
The particle trapping chip according to any one of [20] to [22], in which
the wells in the particle trapping region are arranged such as to form a plurality of rows or columns, and two adjacent rows or columns have mutually different label elements.

[24]
A particle analyzing system including:
a particle trapping chip that includes a particle trapping region having at least one well, each of the at least one well having a label element capable of being transferred from the well to a particle;
a particle recovering section that recovers the particle discharged from the at least one well; and
an identification information acquiring section that acquires identification information possessed by the discharged particle.

REFERENCE SIGNS LIST

100 Particle trapping chamber
101 Particle trapping chip
104 Particle trapping region
105 Well
108 Particle

The invention claimed is:
1. A particle confirming method comprising:
a trapping step of trapping a particle through a linker fixed to a well in a plurality of wells in a particle trapping region, comprising:
a labeling step of labeling the particle trapped in the well to impart identification information to the particle, comprising:
coupling a photodegradable linker to the well;
coupling a first fluorescent substance and a second fluorescent substance to a label element holding substance;
coupling the label element holding substance to the linker fixed to the well;
adding a particle to the well;
irradiating the well with excitation light, wherein after being irradiated with excitation light the first fluorescent substance extinguishes and attaches to the particle and the second fluorescent substance extinguishes more slowly than the first substance and the second fluorescent substance is coupled to the particle to provide a label element and impart identification information to the particle;
a correlating step of correlating identification information possessed by the particle trapped in the well in the particle trapping region with position information of the well;
a discharging step of discharging the particle from the well after the correlating step;
an identification information acquiring step of acquiring identification information of the particle after the discharging step; and
a confirming step of confirming whether the particle has been trapped in the well possessing the position information after the discharging step, comprising:
comparing the acquired identification information of the particle after the discharging step with the position information of the well;
if the acquired identification information of the particle after the discharging step matches the position information of the well,
confirming that the particle had been trapped in the well.

2. The particle confirming method according to claim 1, wherein
the particle trapping region contains the plurality of wells and in the labeling step, adjacent wells in the particle trapping region have label elements with different identification information, and the particles trapped in the adjacent wells are labeled with different label elements having different identification information.

3. The particle confirming method according to claim 1, wherein
in the labeling step, wells in the particle trapping region are arranged to form a plurality of rows or columns, adjacent two rows or columns have mutually different label elements with mutually different identification information, and particles trapped in the wells in the adjacent rows or columns are labeled with the different label elements having mutually different identification information.

4. The particle confirming method according to claim 1, wherein
the correlating step further includes an image acquiring step of acquiring an image of the particle trapping region, and
a color, or a size or shape of the particle is acquired from the image as additional identification information and correlated the position information.

5. The particle confirming method according to claim 1, wherein
the particle trapping region is divided into a plurality of fields, and
the label element is for specifying the field in which the well is disposed.

6. The particle confirming method according to claim 1, wherein the discharging step further includes a light irradiation step of irradiating the linker fixed to the well with light to cut the linker.

7. The particle confirming method according to claim 1, wherein
the particle confirming method further includes a particle moving step of causing the particle discharged from the well in the discharging step to pass through a channel, and
in the identification information acquiring step, the identification information is acquired from the particle passing through the channel or the particle having passed through the channel.

8. The particle confirming method according to claim 1, wherein
in the confirming step, a predetermined number of successive particles is disposed of when an order of identification information of the particles discharged in the discharging step and an order of identification information of the particles acquired in the identification information acquiring step are different from each other.

9. The particle confirming method according to claim 1, further comprising:
a particle sorting step.

10. The particle confirming method according to claim 1, wherein
in the discharging step, a plurality of particles each having identification information is discharged successively.

11. The particle confirming method according to claim 10, wherein
in the confirming step, an order of discharge of the plurality of particles is determined.

12. The particle confirming method according to claim 10, wherein
in the discharging step, the discharge is temporarily stopped after a predetermined number of particles are discharged successively.

13. The particle confirming method according to claim 10, wherein
in the discharging step, a particle having a known identification information is used as to be a mark that is discharged after a predetermined number of particles are discharged successively.

14. The particle confirming method according to claim 10, wherein
in the discharging step, two or more particles discharged successively have different pieces of identification information.

* * * * *